(12) United States Patent
Coruzzi et al.

(10) Patent No.: US 6,864,405 B1
(45) Date of Patent: Mar. 8, 2005

(54) TRANSGENIC PLANTS THAT EXHIBIT ENHANCED NITROGEN ASSIMILATION

(75) Inventors: Gloria M. Coruzzi, New York, NY (US); Timothy Brears, Durham, NC (US)

(73) Assignee: New York University, New York, NY (US)

(*) Notice: Subject to any disclaimer, the term of this patent is extended or adjusted under 35 U.S.C. 154(b) by 257 days.

(21) Appl. No.: 09/605,521

(22) Filed: Jun. 27, 2000

Related U.S. Application Data

(60) Division of application No. 08/987,237, filed on Dec. 9, 1997, now Pat. No. 6,107,547, which is a continuation of application No. 08/319,176, filed on Oct. 6, 1994, now abandoned, which is a continuation-in-part of application No. 08/132,334, filed on Oct. 6, 1993, now abandoned.

(51) Int. Cl.$^7$ .......................... A01H 1/00; A01H 11/00; C12N 15/82; C07H 21/02; C01H 21/04
(52) U.S. Cl. .......................... 800/290; 435/6; 435/468; 536/23.1; 536/23.2; 800/295
(58) Field of Search ................................ 435/419, 468, 435/69.1; 536/236; 800/290, 278, 298

(56) References Cited

FOREIGN PATENT DOCUMENTS

| AU | A-17321/88 | 6/1988 |
|---|---|---|
| EP | 0303780 A2 | 5/1988 |
| WO | WO86/02097 | 4/1986 |
| WO | WO 90/13633 | 11/1990 |
| WO | 91-11524 | 8/1991 |

OTHER PUBLICATIONS

Jorgensen, Trends in Biotechnology, 1990, vol. 8, pp 340–344.*
Bennett et al. 1989, Plant Mol. Biol. 12:553–565.
Brears T., 1993, Plant Physiology 103:1285–1290.
Brears et al., 1991, The Plants Journal, vol. 1, pp. 235–244.
Cullimore et al. 1983, Planta 157:245–253.
Dickson et al., 1992, Plant Mol. Biol. 20:333–336.
Dilworth and Dure, 1978, Plant Physiol 61:698–702.
Donn et al., 1984, J. Molec. Appl. Genet. 2:621–635.
Eckes et al., 1989, Mol. Gen. Genet. 217:263–268.
Edwards and Coruzzi, 1989, Plant Cell 1:241–248.
Edwards et al., 1990, Proc. Natl. Acad. Sci. USA 87:3459–3463.
Foyer et al., 1994, *Biochemical Society Transactions* 22(4):909–915.
Gebhardt et al. 1986, EMBO J. 5:1429–1435.
Givan et al., 1988, TIBS 13:433–437.
Hemon et al., 1990, Plant Mol. Biol. 15:895–904.
Herskowitz, 1987, Nature 329:219–222
Hirel et al., 1992, Plant Mol. Biol. 20:207–218.
Keys et al., 1978, Nature, 275:741–743.
Knight and Langston–Unkefer, 1988, Science 241:951–954.
Lea and Forde, 1994, Plant Molecular Biology, 17:541–556.
Lea and Fowden, 1975, Proc. R. Soc. Lond. 192:13–26.
Lea and Joy, 1983, Amino acid interconversion in germinating seeds. In: *Recent Advances in Phythochemistry: Mobilization of Reserves in Germination*, ed. Nozolillo et al., Plenum Press, p. 77–109.
Lough et al, 1992, Plant Mol. Biol. 19:391–399.
McNally et al., 1983, Plant Physiol. 72:22–25.
Napoli et al., 1990, Plant Cell 2:279–289.
Oaks and Hirel, 1985, Ann. Rev. Plant Physiol. 36:345–365.
Oaks and Ross, 1984, Can. J. Bot. 62:68–73.
Peterman and Goodman, 1991, Mol. Gen. Genet. 230:145–154.
Pfeiffer et al., 1986, J. Biol. Chem. 261:1914–1919.
Pfeiffer et al., 1987, J. Biol. Chem. 262:11565–11570.
Rognes, 1975, Phytochemistry, 14:1975–1982.
Sieciechowicz et al., 1988, Phytochemistry 27:663–671.
Stulen and Oaks, 1977, Plant Physiol. 60:680–683.
Ta et al., 1984, Plant Physiol 74:822–826.
Temple et al., 1993, Mol. Gen. Genet. 236:315–325.
Tingey et al., 1987, EMBO J. 6:1–9.
Tingey et al., 1988, J. Biol. Chem. 263:9651–9657.
Tsai and Coruzzi, 1990, EMBO J. 9:323–332.
Tsai and Coruzzi, 1991, Mol Cell Biol. 11:4966–4972.
Tsai and Coruzzi, Transgenic Plants for Studying Genes Encoding Amino Acid Biosynthetic Enzymes, in *Transgenic Plants*, vol. 1, Kung and Wu eds., Academic Press, San Diego, CA, (1993) p. 181–194.
Udvardi and Kahn, 1991, Mol. Gen. Genet. 231:97–105.
van der Krol et al., 1990, Plant Cell 2:291–299.
Wallsgrove et al., 1983, Plant Cell Environ. 6:301–309.
Wallsgrove et al., 1987, Plant Physiol. 83:155–158.
Walker and Coruzzi, 1989, Plant Physiol. 91:702–708.
Zehnacker et al., 1992, Planta 187:266–274.

* cited by examiner

Primary Examiner—Ram R. Shukla
Assistant Examiner—Jane Zara
(74) Attorney, Agent, or Firm—Jones Day

(57) ABSTRACT

The present invention relates to a method for producing plants with improved agronomic and nutritional traits. Such traits include enhanced nitrogen assimilatory and utilization capacities, faster and more vigorous growth, greater vegetative and reproductive yields, and enriched or altered nitrogen content in vegetative and reproductive parts. More particularly, the invention relates to the engineering of plants modified to have altered expression of key enzymes in the nitrogen assimilation and utilization pathways. In one embodiment of the present invention, the desired altered expression is accomplished by engineering the plant for ectopic overexpression of one of more the native or modified nitrogen assimilatory enzymes. The invention also has a number of other embodiments, all of which are disclosed herein.

11 Claims, 10 Drawing Sheets

Figure 1:
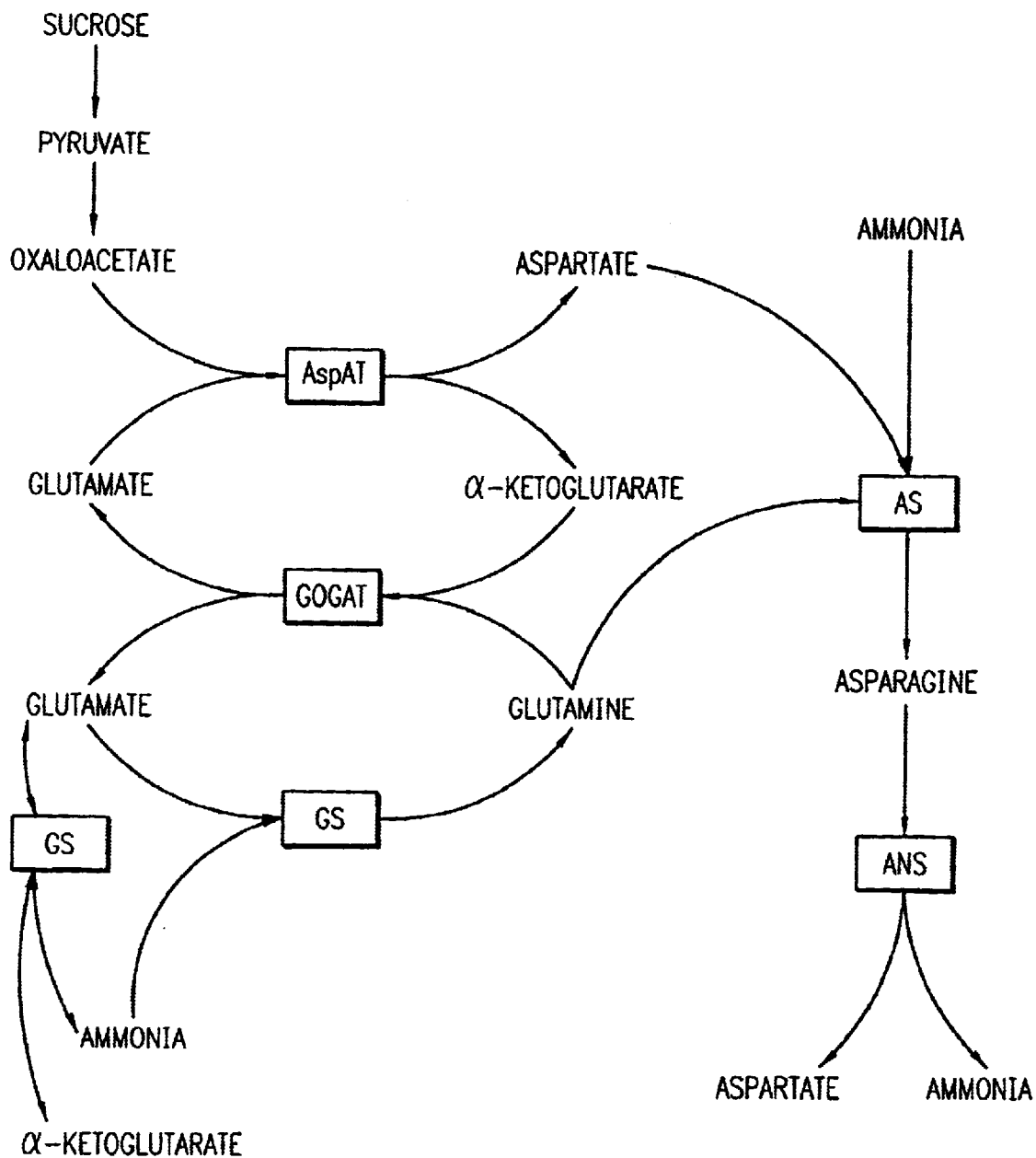

FIG. 12
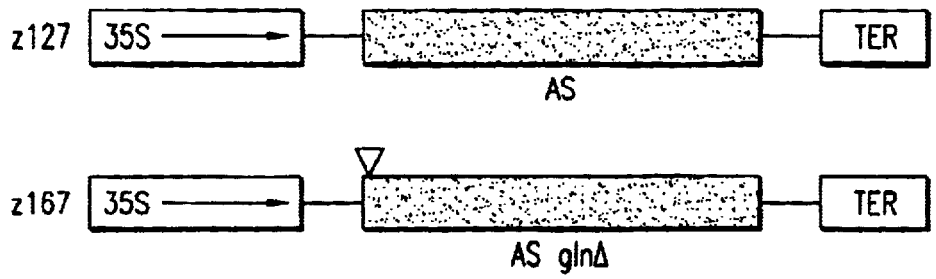
FIG. 13
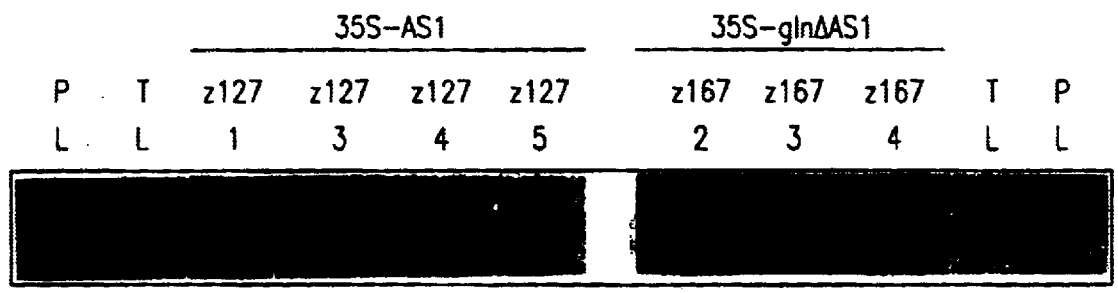
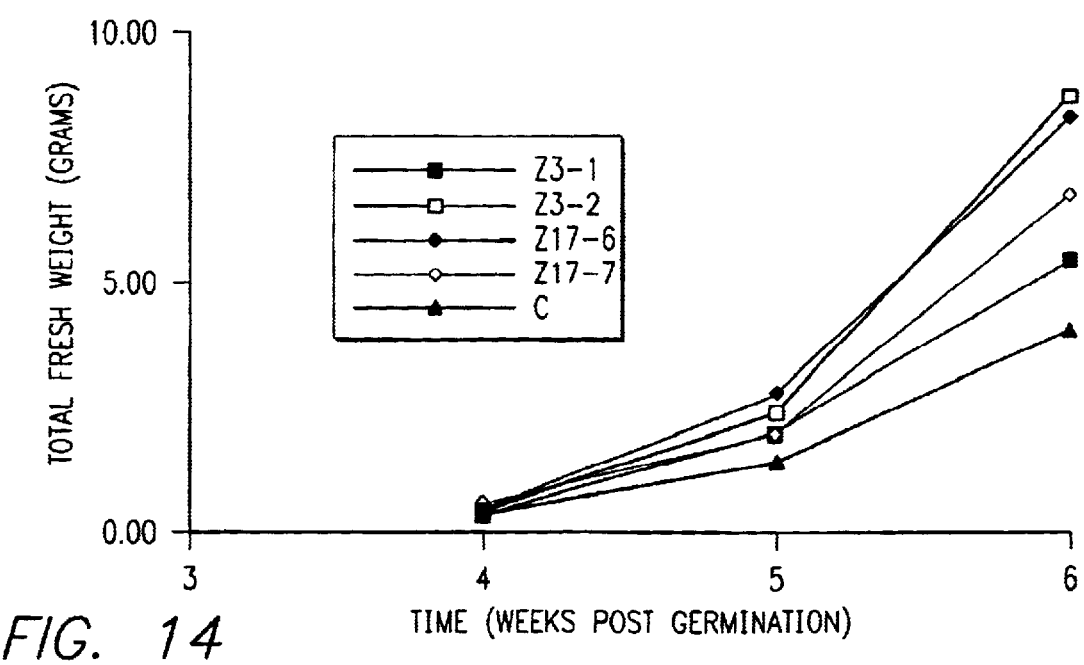
FIG. 14

TRANSGENIC PLANTS THAT EXHIBIT ENHANCED NITROGEN ASSIMILATION

This application is a division of application Ser. No. 08/987,237, filed Dec. 9, 1997 currently issued as U.S. Pat. No. 6,107,547, which is continuation of application Ser. No. 08/319,176 filed Oct. 6, 1994 (abandoned), which is a continuation-in-part of application Ser. No. 08/132,334 filed Oct. 6, 1993 (abandoned), the disclosures of application Ser. No. 08/132,334 and 08/319,176 are hereby incorporated by reference in their entirety.

This invention was made with government support under grant no.:GM32877 awarded by the National Institute of Health, and grant nos.:DEFG0292 and ER20071 awarded by the Department of Energy. The government has certain rights in the invention.

1. INTRODUCTION

The present invention relates generally to genetic-engineering plants to display enhanced nitrogen assimilatory and utilization capacities, grow larger, more efficiently or rapidly, and/or have enriched nitrogen contents in vegetative and/or reproductive plant parts and/or increased biomass. More particularly, this invention relates to producing transgenic plants engineered to have altered expression of key enzymes in the nitrogen assimilation and utilization pathways. The engineered plants may be productively cultivated under conditions of low nitrogen fertilizer input or in nitrogen poor soils. Alternatively, the engineered plants may be used to achieve faster growing or maturing crops, higher crop yields and/or more nutritious products under ideal cultivation conditions.

2. BACKGROUND OF THE INVENTION

Nitrogen is often the rate-limiting element in plant growth and all field crops have a fundamental dependence on inorganic nitrogenous fertilizer. Since fertilizer is rapidly depleted from most soil types, it must be supplied to growing crops two or three times during the growing season. Nitrogenous fertilizer, which is usually supplied as ammonium nitrate, potassium nitrate, or urea, typically accounts for 40% of the costs associated with crops such as corn and wheat. It has been estimated that approximately 11 million tons of nitrogenous fertilizer is used in both North America and Western Europe annually, costing farmers $2.2 billion each year (Sheldrick, 1987, World Nitrogen Survey, Technical Paper no. 59, Washington, D.C.). Furthermore, World Bank projections suggest that annual nitrogen fertilizer demand worldwide will increase from around 90 million tons to well over 130 million tons over the next ten years. Increased use efficiency of nitrogen by plants should enable crops to be cultivated with lower fertilizer input, or alternatively on soils of poorer quality and would therefore have significant economic impact in both developed and developing agricultural systems.

Using conventional selection techniques plant breeders have attempted to improve nitrogen use efficiency by exploiting the variation available in natural populations of corn; wheat, rice and other crop species. There are, however, considerable difficulties associated with the screening of extensive populations in conventional breeding programs for traits which are difficult to assess under field conditions, and such selection strategies have been largely unsuccessful.

2.1. Nitrogen Assimilatory Pathway in Plants

Plants obtain nitrogen from their environment in the form of inorganic compounds, namely nitrate and ammonia taken up from roots, and atmospheric $N_2$ reduced to ammonia in nitrogen-fixing root nodules. Although some nitrate and ammonia can be detected in the transporting vessels (xylem and phloem), the majority of nitrogen is first assimilated into organic form (e.g., amino acids) which are then transported within the plant.

The first step in the assimilation of inorganic nitrogen into organic form predominately involves the incorporation of ammonia with glutamate to form glutamine, catalyzed by the enzyme, glutamine synthetase (GS; EC 6.3.1.2). Glutamine thus formed may in turn donate its amide group in the formation of asparagine, catalyzed by the enzyme, asparagine synthetase (AS; E.C. 6.3.5.4). The steady flow of nitrogen from ammonia to asparagine in this pathway depends upon the recycling of glutamate and α-ketoglutarate and aspartate, catalyzed by glutamine 2:oxoglutarate aminotransferase (GOGAT; E.C.) and aspartate aminotransferase (AspAT; E.C.), respectively (see FIG. 1). Thus, GS, AS, AspAT and GOGAT comprise the key enzymes of the main nitrogen assimilatory pathway of higher plants.

Evidence exists indicating that ammonia incorporation may proceed through alternative pathways other than that catalyzed by GS (FIG. 1). See Knight and Langston-Unkefer, 1988, Science 241:951–954. One pathway may involve the incorporation of ammonia with α-ketoglutarate to form glutamate, catalyzed by glutamate dehydrogenase (GDH). Another pathway may involve the incorporation of ammonia with aspartate to form asparagine, catalyzed by asparagine synthetase (Oaks and Ross, 1984, Can. J. Bot. 62:68–73; Stulen and Oaks, 1977, Plant Physiol. 60:680–683). Since both of these enzymes (GDH and AS) have a high Km for ammonia, the roles of these alternative nitrogen assimilation pathways under normal growth conditions (e.g., low concentrations of internal ammonia) remain unclear. One study suggests these or other alternative nitrogen assimilation pathways may make significant contributions to a plant's nitrogen assimilation capacity when intracellular ammonium concentration is elevated above normal levels (Knight and Langston-Unkefer, id.).

2.2. Nitrogen Transport and Utilization

Glutamine and asparagine represent the major long-distance nitrogen transport compounds in plants and are abundant in phloem sap. Aside from their common roles as nitrogen carriers, these two amino acids have somewhat different roles in plant nitrogen metabolism. Glutamine is the more metabolically active of the two and can directly donate its amide nitrogen to a large number of substrates in various anabolic reactions. Because of its reactivity, glutamine is generally not used by plants to store nitrogen.

By contrast, asparagine is a more efficient compound for nitrogen transport and storage compared to glutamine because of its higher N:C ratio. Furthermore, asparagine is also more stable than glutamine and can accumulate to higher levels in vacuoles. Indeed, in plants that have high nitrogen assimilatory capacities, asparagine appears to play a dominant role in the transport and metabolism of nitrogen. See Lea and Miflin, Transport and metabolism of asparagine and other nitrogen compounds within the plant, in *The Biochemistry of Plants: A Comprehensive Treatise. vol 5. Amino acid and derivatives*, Miflin ed., Academic Press, New York (1980) pp 569–607; and Sieciechowicz et al., 1988, Phytochemistry 27:663–671. Because of its relative stability, asparagine does not directly participate in nitrogen metabolism, but must be first hydrolyzed by the enzyme asparaginase (ANS; E.C. 3.5.1.1) to produce aspartate and ammonia which then could be utilized in synthesis of amino acids and proteins (See FIG. 1).

2.3. Plant Genes Involved in Nitrogen Assimilation and Utilization

Many of the genes encoding enzymes involved in plant nitrogen assimilation and utilization have been cloned and studied. See Tsai and Coruzzi, Transgenic Plants for Studying Genes Encoding Amino Acid Biosynthetic Enzymes, in *Transgenic Plants*, Vol. 1, Kung and Wu eds., Academic Press, San Diego, Calif., (1993) pg 181–194, and references cited therein for discussions of plant glutamine synthetase (GS) and asparagine synthetase (AS) genes; Udvardi and Kahn, 1991, Mol. Gen. Genet. 231:97–105, for a discussion of the alfalfa aspartate aminotransferase gene; Zehnacker et al., 1992, Planta 187:266–274, for a discussion of the tobacco glutamate 2: oxoglutarate aminotransferase (GOGAT, also known as glutamate synthetase) gene; Lough et al, 1992, Plant Mol. Biol. 19:391–399, and Dickson et al., 1992, Plant Mol. Biol. 20:333–336, for discussions of lupin asparaginase gene.

Among the plant nitrogen assimilation and utilization genes, the most extensively studied are the glutamine synthetase and asparagine synthetase genes. Multiple genes exist for GS and AS, and molecular characterization of these genes has shown that they have different expression patterns.

2.3.1. Glutamine Synthetase Genes

GS is active in a number of organs during plant development (McNally et al., 1983, Plant Physiol. 72:22–25). In roots it assimilates ammonia derived from soil water (Oaks and Hirel, 1985, Ann. Rev. Plant Physiol. 36:345–365), and in root nodules of legumes, GS assimilates ammonia fixed by rhizobia (Cullimore et al. 1983, Planta 157:245–253). In cotyledons GS reassimilates nitrogenous reserves mobilized during germination (Lea and Joy, 1983,Amino acid interconversion in germinating seeds. In: *Recent Advances in Phythochemistry: Mobilization of Reserves in Germination*, ed. Nozolillo et al., Plenum Press, p. 77–109), and in leaves chloroplastic GS2 assimilates ammonia released in photorespiration (Givan et al. 1988, TIBS 13:433–437). The various roles of GS are undertaken by different GS isoforms which are derived from different genes that are expressed differentially (Gebhardt et al. 1986, EMBO J. 5:1429–1435; Tingey et al. 1987, EMBO J. 6:1–9).

In pea, Phaseolus, and Arabidopsis, chloroplastic GS2 is encoded by a single nuclear gene, whereas multiple genes for cytosolic GS exist in each of these species (Bennett et al. 1989, Plant Mol. Biol. 12:553–565; Tingey et al. 1988, J. Biol. Chem. 263:9651–9657; Peterman and Goodman, 1991, Mol. Gen. Genet. 230:145–154). The analysis of the expression of these GS genes in vivo and in transgenic host plants has helped unravel the roles of the various GS isoforms in plant nitrogen metabolism.

The GS gene family in pea comprises four distinct but homologous nuclear genes. Three encode cytosolic GS isoforms, and one encodes the chloroplastic GS2 isoform (Tingey et al., 1987, EMBO J. 6:1–9; Tingey et al., 1988, J. Biol. Chem. 263:9651–9657). Northern blot analysis has demonstrated that the gene for chloroplastic GS2 is expressed in leaves in a light-dependent fashion due in part to phytochrome and in part to photorespiratory effects (Edwards and Coruzzi, 1989, Plant Cell 1:241–248). The three genes for cytosolic GS (GS1, GS3A and GS3B) also appear to serve distinct roles. In roots cytosolic GS1 is the predominant isoform, although it is also expressed in nodules. Cytosolic GS3A and GS3B are highly expressed in nodules and also in cotyledons of germinating seeds (Tingey et al., 1987, EMBO J. 6:1–9; Walker and Coruzzi, 1989, Plant Physiol. 91:702–708). While the GS3A and GS38 genes are near identical in sequence, gene specific S1-nuclease analysis has revealed that GS3A expression is consistently higher than that of GS3B (Walker and Coruzzi, 1989, Plant Physiol. 91:702–708). Using promoter-GUS fusions and transgenic plant analysis it has been shown that chloroplastic GS2 is expressed only in photosynthetic cell-types and that cytosolic GS3A is expressed exclusively in the phloem cells of the vasculature in most organs. GS3A is also strongly expressed in root and nodule meristems (Edwards et al., 1990, Proc. Natl. Acad. Sci. USA. 87:3459–3463; Brears et al., 1991, *The Plant Journal*, vol. 1, pp. 235–244). From the tightly controlled regulation at cell-type and organ level it appears that the various genes for GS fulfill non-overlapping roles in ammonia assimilation.

2.3.2. Asparagine Synthetase Genes

Two AS genes have been cloned from pea (AS1 and AS2); both are expressed at highest levels in root nodules and cotyledons. AS1 and AS2 are both expressed in roots. AS2 is expressed constitutively in roots, while AS1 is expressed only in roots of dark-grown plants (Tsai and Coruzzi, 1990, EMBO J 9:323–332). Furthermore, AS1 and AS2 are expressed in mature leaves of dark-adapted plants, whereas their expression is inhibited by light. This high level of AS gene expression in the dark corresponds to the use of asparagine as a long-distance nitrogen transport compound synthesized under conditions of reduced availability of photosynthetic carbon (asparagine has a higher N:C ratio than glutamine). Studies of AS1 promoter-GUS fusions in transgenic plants have shown that the AS1 gene, like the GS3A gene, is also expressed exclusively in phloem cells. From the tightly controlled regulation at cell-type and organ level, it seems that the various AS genes may also fulfill non-overlapping roles in plant nitrogen metabolism.

2.4. Genetic Engineering of Nitrogen Assimilation and Utilization Processes in Plants In plants, genetic engineering of nitrogen assimilation processes has yielded varied results. In one case, expressing a prokaryotic ammonium dependent asparagine synthetase (ASN-A) gene in tobacco conferred resistance to various glutamine synthetase (GS) inhibitors (Dudits et al., *Transgenic Plants expressing a prokaryotic ammonium dependent asparagine synthetase*, WO 9111524, Aug. 8, 1991). These same plants also exhibited a number of growth alterations including increased growth rate, accelerated plant development, early flower development and increased green mass and plant dry weight. The growth effect of ASN-A expression is paradoxical as GS inhibitor treatments enhanced rather than attenuated growth in the engineered plants.

By contrast, numerous studies examining overexpression of glutamine synthetase (GS) have failed to report any positive effect of the overexpression on plant growth. See Lea and Forde, 1994, Plant Molec. Biol. 17:541–558; Eckes et al., 1989, Molec. Gen. Genet. 217:263–268 (transgenic tobacco plants overexpressing alfalfa GS); Hemon et al., 1990, Plant Mol. Biol. 15:895–904 (transgenic tobacco plants overexpressing bean GS in the cytoplasm or mitochondria); Hirel et al., 1992, Plant Mol. Biol. 20:207–218 (transgenic tobacco plants overexpressing soybean GS in tobacco plants). One study has reported observing increases in total soluble protein content in transgenic tobacco plants overexpressing the alfalfa GS1 gene.

However, since this same study also reported similar increases in total soluble protein content in transgenic tobacco plants expressing antisense RNA to the GS1 gene, the relationship between GS1 expression and the increase in soluble protein appears unclear (Temple et al., 1993, Mol. Gen. Genet. 236:315–325). One clearly established effect of GS overexpression in plants is resistance to phosphinothricin, a GS inhibiting herbicide (Eckes et al. ibid.; Donn et al., 1984, J. Molec. Appl. Genet. 2:621–635 (a phosphinothricin-resistant alfalfa cell line contained amplification of the GS gene)). There also has been a claim that plants engineered with overexpression of an alfalfa GS gene grow more rapidly than unengineered plants (Eckes et al., 1988, Australian Patent Office Document No.: AU-A-17321/88). The claimed faster growth, however, occurs only under low- but not normal- or high- nitrogen growth conditions. Moreover, it is unclear whether the faster growth produce mature plants with greater biomass or reproductive yield. Compare id. with Eckes et al., 1989, Molec. Gen. Genet. 217:263–268.

3. SUMMARY OF THE INVENTION

The present invention relates to the production of transgenic plants with altered expression levels and/or cell-specific patterns of expression of key enzymes involved in nitrogen assimilation and utilization (The respective roles of these enzymes are shown in FIG. 1) so that the resulting plants have enhanced nitrogen assimilation and/or utilization capacities as well as improved agronomic characteristics. The present invention particularly relates to altering the expression of glutamine synthetases, asparagine synthetases, glutamate 2:oxoglutarate aminotransferases (glutamate 2:oxoglutarate aminotransferase is also known as glutamate synthetase), aspartate aminotransferases, glutamate dehydrogenases and asparaginases (see FIG. 1).

The invention has utility in improving important agronomic characteristics of crop plants. One of the improvements would be the ability of the engineered plants to be productively cultivated with lower nitrogen fertilizer inputs and on nitrogen-poor soil. Additional improvements include more vigorous (i.e., faster) growth as well as greater vegetative and/or reproductive yield under normal cultivation conditions (i.e., non-limiting nutrient conditions). To achieve these same improvements, traditional crop breeding methods would require screening large segregating populations. The present invention circumvent the need for such large scale screening by producing plants many of which, if not most, would have the desired characteristics.

According to the present invention, achieving the desired plant improvements may require, in some instances, the ectopic overexpression of a single gene or multiple genes encoding nitrogen assimilation or utilization enzyme(s). The modified expression may involve engineering the plant with any or several of the following: a) a transgene in which the coding sequence for the enzyme is operably associated to a strong, constitutive promoter; b) additional copies of the native gene encoding the desired enzyme; c) regulatory gene(s) that activates the expression of the desired gene(s) for nitrogen assimilation or utilization; d) a copy of the native gene that has its regulatory region modified for enhanced expression; and e) a transgene which expresses a mutated, altered or chimeric version of a nitrogen assimilation or utilization enzyme.

In other instances, achieving the desired plant improvements may require altering the expression pattern of a nitrogen assimilation or utilization enzyme. The altered expression pattern may involve engineering the plant with any or many of the following: a) a transgene in which the coding sequence for the enzyme is operably associated to a promoter with the desired expression pattern (such promoters may include those considered to have tissue or developmental-specific expression patterns); b) modified regulatory genes that activates the expression of the enzyme-encoding gene in the preferred pattern; c) a native copy of the enzyme-encoding gene that has its regulatory region modified to express in the preferred pattern.

In yet other instances, achieving the desired plant improvements may require suppressing the expression level and/or pattern of a nitrogen assimilation or utilization enzyme. The suppression of expression may involve engineering the plant with genes encoding antisense RNAs, ribozymes, co-suppression constructs, or "dominant negative" mutations (see Herskowitz, 1987, Nature 329:219–222 for an explanation of the mechanism of gene suppression by dominant negative mutations). Further, gene suppression may also be achieved by engineering the plant with a homologous recombination construct that replaces the native gene with a copy of a defective gene or enzyme-encoding sequence that is under the control of a promoter with the desired expression level and/or pattern.

In still other instances, achieving the desired plant improvements may require expressing altered or different forms of the enzymes in the nitrogen assimilation or utilization pathways. Such efforts may involve developing a plant-expressible gene encoding a nitrogen assimilation or utilization enzyme with catalytic properties different from those of the corresponding host plant enzymes and engineering plants with that gene construct. Gene sequences encoding such enzymes may be obtained from a variety of sources, including, but not limited to bacteria, yeast, algae, animals, and plants. In some cases, such coding sequences may be directly used in the construction of plant-expressible gene fusions by operably linking the sequence with a desired plant-active promoter. In other cases, the utilization of such coding sequences in gene fusions may require prior modification by in vitro mutagenesis or de novo synthesis to enhance their translatability in the host plant or to alter the catalytic properties of the enzymes encoded thereon. Useful alterations may include, but are not limited to, modifications of residues involved in substrate binding and/or catalysis. Desired alterations may also include the construction of hybrid enzymes. For instance, the different domains of related enzymes from the same organism or different organisms may be recombined to form enzymes with novel properties.

In all instances, a plant with the desired improvement can be isolated by screening the engineered plants for altered expression pattern or level of the nitrogen assimilation or utilization enzyme, altered expression pattern or level of the corresponding mRNA or protein, altered nitrogen assimilation or utilization capacities, increased growth rate, enhanced vegetative yield, or improved reproductive yields (e.g., more or larger seeds or fruits). The screening of the engineered plants may involve enzymatic assays and immunoassays to measure enzyme/protein levels; Northern analysis, RNase protection, primer extension, reverse transcriptase/PCR, etc. to measure mRNA levels; measuring the amino acid composition, free amino acid pool or total nitrogen content of various plant tissues; measuring growth rates in terms of fresh weight gains over time; or measuring plant yield in terms of total dry weight and/or total seed weight.

The present invention is based, in part, on the surprising finding that enhancing the expression of nitrogen assimilation or utilization enzymes in plants resulted in enhanced growth characteristics, or improved vegetative or reproductive yields. The invention is illustrated herein by the way of working examples in which tobacco plants were engineered with recombinant constructs encoding a strong, constitutive plant promoter, the cauliflower mosaic virus (CaMV) 35S promoter, operably linked with sequences encoding a pea glutamine synthetase (GS) gene or a pea asparagine synthetase (AS) gene. RNA and protein analyses showed that a majority of the engineered plants exhibited ectopic, overexpression of GS or AS. The GS or AS overexpressing lines have higher nitrogen contents, more vigorous growth characteristics, increased vegetative yields or better seed yields and quality than the control, wild-type plant.

3.1. Definitions

The terms listed below, as used herein, will have the meaning indicated.

| | |
|---|---|
| 35S = | cauliflower mosaic virus promoter for the 35S transcript |
| AS = | Asparagine synthetase |
| AspAT = | aspartate aminotransferase (also known as AAT) |
| CaMV = | Cauliflower Mosaic Virus |
| cDNA = | complementary DNA |
| DNA = | deoxyribonucleic acid |
| GDH = | glutamate dehydrogenase |
| gene fusion = | a gene construct comprising a promoter operably linked to a heterologous gene, wherein said promoter controls the transcription of the heterologous gene |
| GOGAT = | glutamate 2:oxoglutarate aminotransferase (alternately known as glutamate synthetase) |
| Fd-GOGAT = | Ferredoxin-dependent glutamate synthase |
| NADH-GOGAT = | NADH-dependent glutamate synthase |
| GS = | glutamine synthetase |
| heterologous gene = | In the context of gene constructs, a heterologous gene means that the gene is linked to a promoter that said gene is not naturally linked to. The heterologous gene may or may not be from the organism contributing said promoter. The heterologous gene may encode messenger RNA (mRNA), antisense RNA or ribozymes. |
| nitrogen non-limiting growth condition = | A nitrogen non-limiting growth condition is one where the soil or medium contains or receives sufficient amounts of nitrogen nutrients to sustain healthy plant growth. Examples of nitrogen non-limiting growth conditions are provided in section 5.2.3. Moreover, one skilled in the art would recognize what constitutes such soils, media and fertilizer inputs for most species and varieties of important crop and ornamental plants (see section 5.3.). |
| PCR = | polymerase chain reaction |
| Progenitor plant = | untransformed, wild-type plant |
| RNA = | ribonucleic acid |

4. DESCRIPTION OF THE FIGURES

FIG. 1. Pathway of nitrogen assimilation/metabolism in plants. The major route for nitrogen assimilation is via glutamine synthetase (GS) and glutamate synthase (GOGAT). Glutamate dehydrogenase (GDH) is thought to function under conditions of ammonia toxicity in the biosynthetic role, or may provide catalytic amounts of glutamate to fuel the GS/GOGAT cycle. GDH probably is more active in its catalytic role to release ammonia from glutamate (e.g., during germination). Aspartate amino transferase (AspAT) catalyzes a reversible reaction. Asparagine synthetase (AS) has two activities; a glutamine-dependent activity and an ammonia-dependent activity. Asparagine catabolism occurs via asparaginase (ANS) to liberate aspartate and ammonia.

Figure 2:
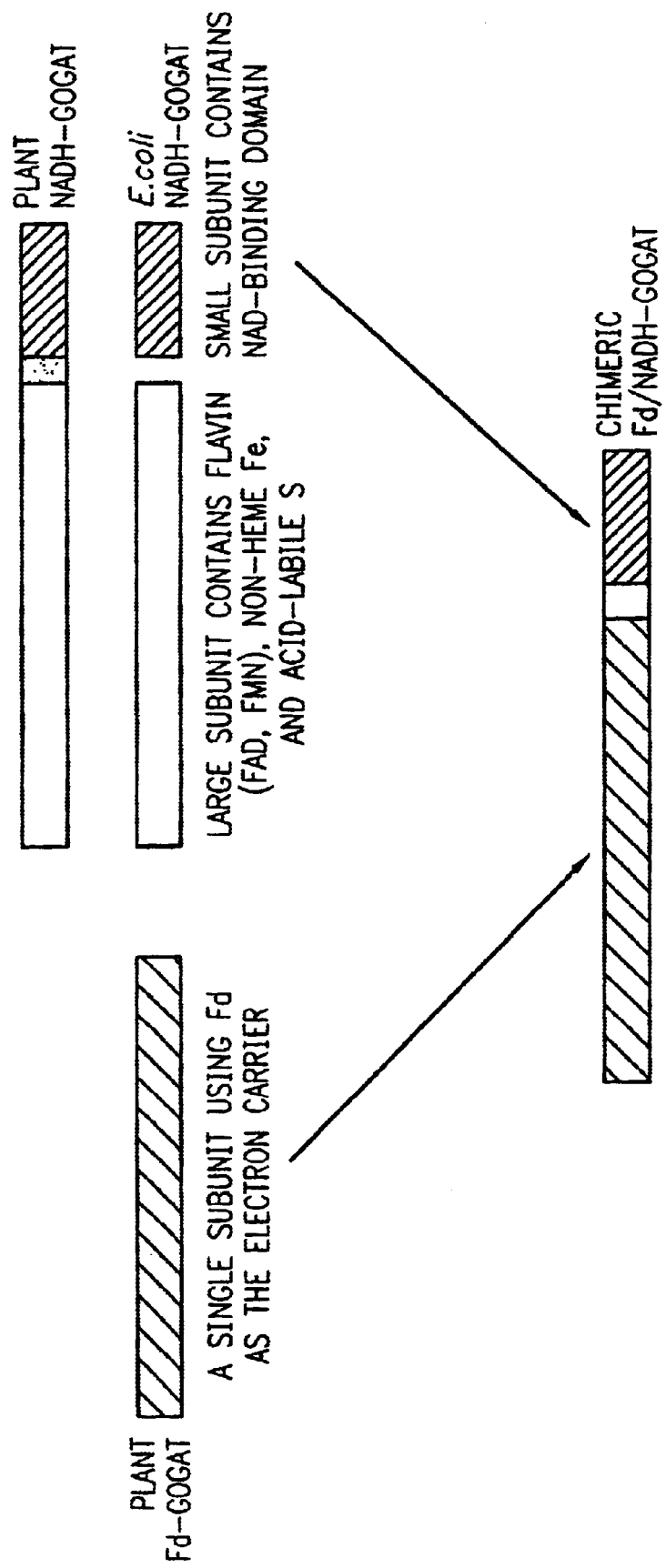

FIG. 2. Engineering a chimeric Fd/NADH GOGAT enzyme. Plant ferredoxin-GOGAT (Fd-GOGAT) large subunit contains Fd-Binding domain (diagonal cross-bars). Plant and *E. coli* NADH-GOGAT: large subunit (open bar), small subunit contains NADH-binding domain (vertical hatches). Chimeric Fd/NADH GOGAT is engineered to contain the large subunit of Fd-GOGAT (Fd-binding domain) plus the small subunit of the NADH-GOGAT of either plant or *E. coli*. The engineering is done by making an in-frame translational fusion of a sequence encoding a plant Fd-GOGAT and a sequence encoding a small subunit of a plant or *E. coli* NADH-GOGAT, containing the NADH-binding domain. The chimeric protein encodes a bispecific or bifunctional GOGAT enzyme which can utilize either Fd or NADH as the reductant.

Figure 3:
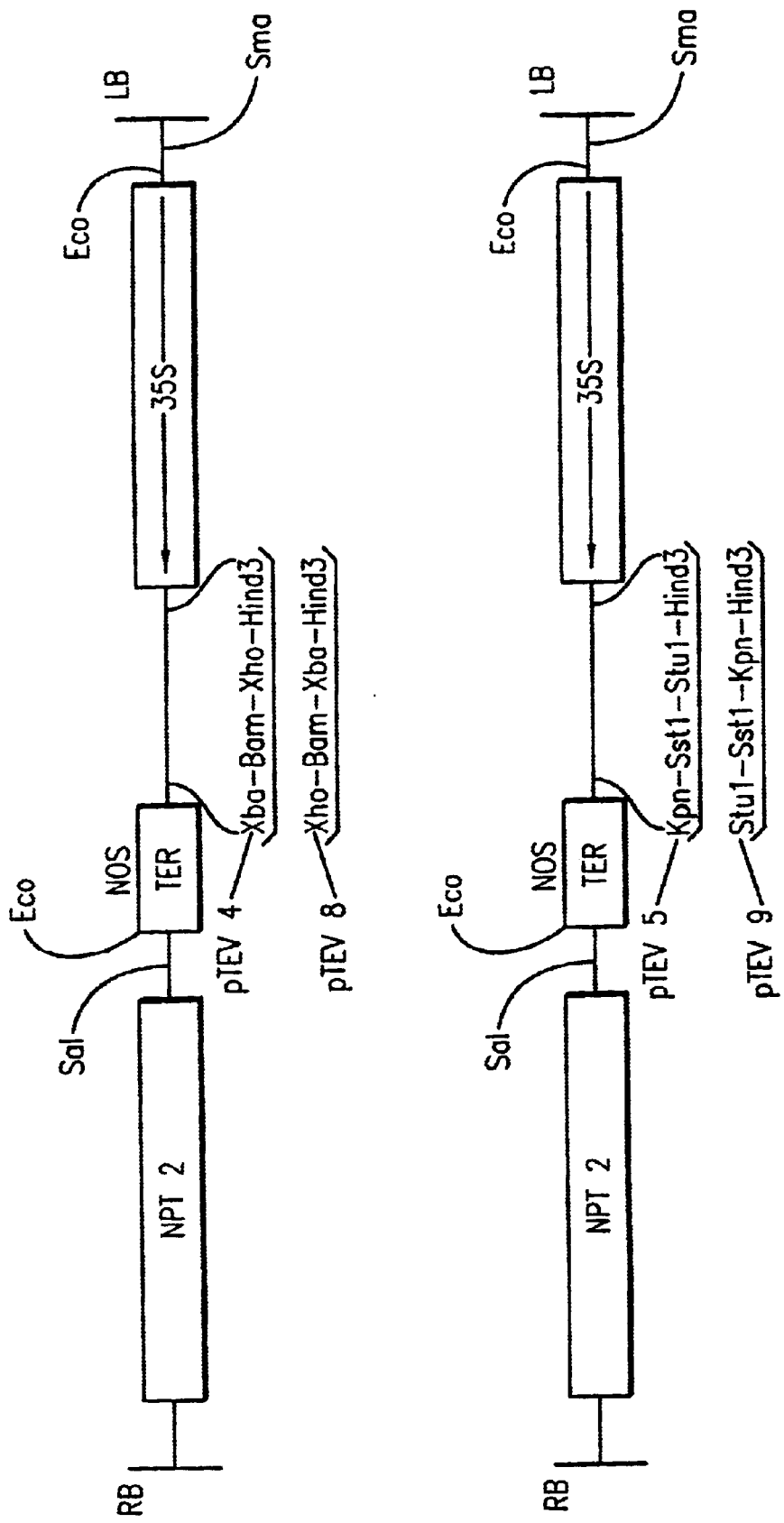

FIG. 3. Maps of Binary Plant Expression Vectors. The binary expression vectors pTEV4, pTEV5, pTEV8 and pTEV9 are derivatives of pBIN19 (Bevan, 1984, Nucleic Acids Res. 12:8711–8721) constructed for the high level expression of cDNAs in transgenic tobacco. For details of construction see Section 6.1.1.

Figure 4:
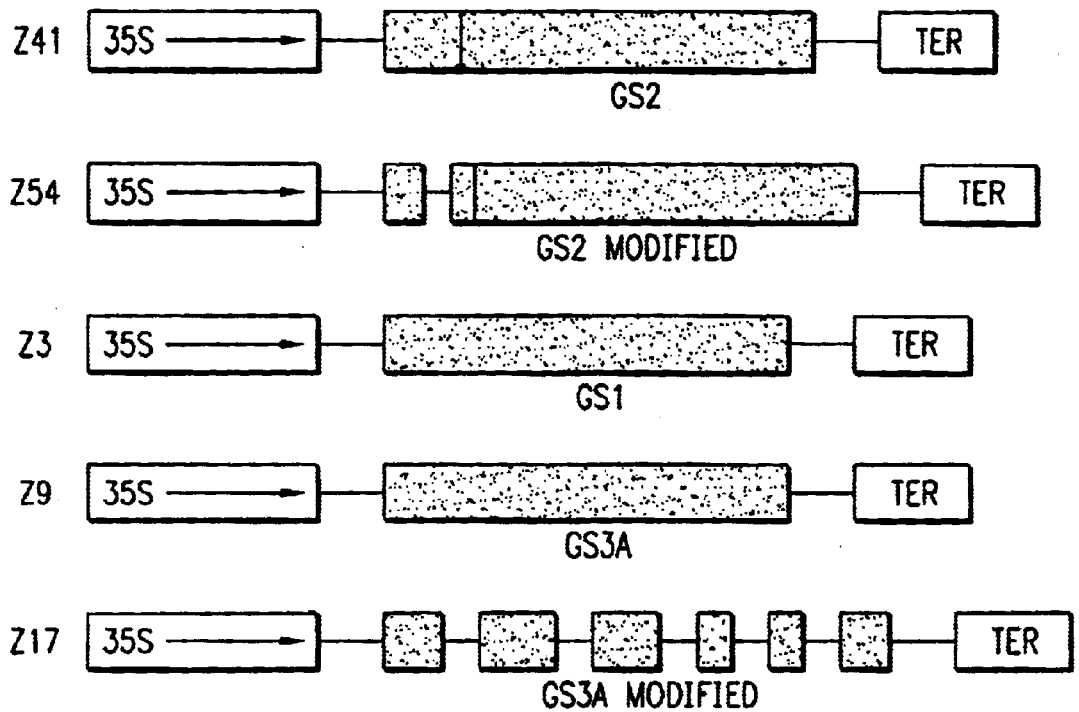

FIG. 4. Chimeric 35S CaMV-GS cDNA Constructs Transferred to Transgenic Tobacco. Pea GS cDNAs were cloned into pTEV expression vectors (see FIG. 3, and Section 6.1.1) for expression behind the Strasbourg strain CaMV 35S promoter (35S). For GS3A and GS2, "modified" clones were constructed incorporating introns from the genomic sequence into the cDNAs (see Section 6.1.2.). Sources of the GS cDNA clones were: GS2 (also known as (aka) GS185); GS1 (aka GS299); GS3A (aka GS341) (Tingey et al., 1988, J. Biol. Chem. 263:9651–9657; Tingey et al., 1987, EMBO J. 6:1–9).

Figure 5:
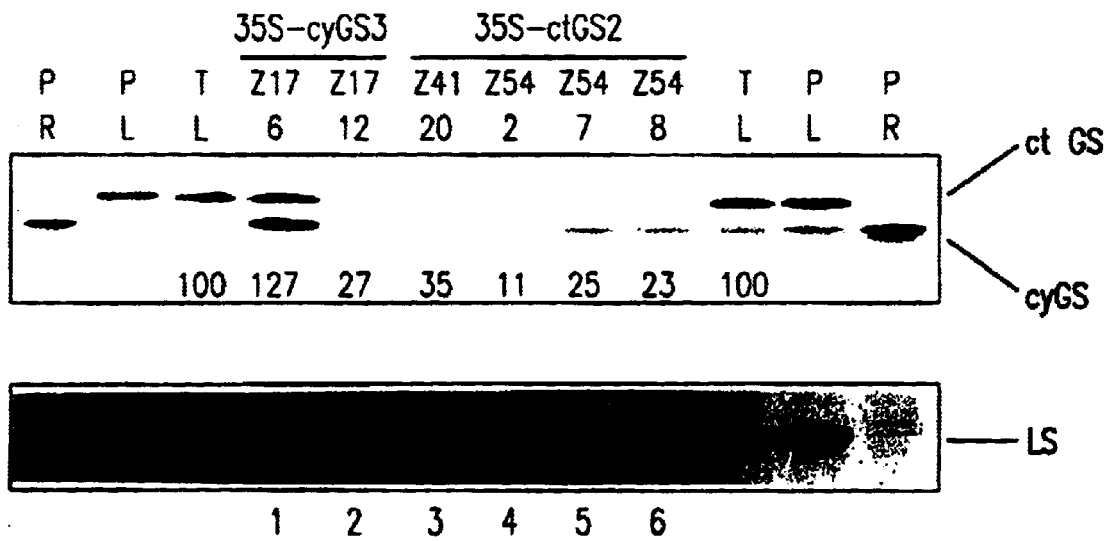

FIG. 5. Analysis of GS Protein in Primary (T1) Transformants Containing GS Transgenes. Top panel: Western analysis of GS polypeptides in primary transformants. Lanes 1 and 2: primary transformants Z17-6 and Z17-12 carrying the cytosolic GS3A gene show overexpression and co-suppression phenotypes respectively. Lanes 3–6: primary transformants Z41-20, Z54-2, Z54-7, and Z54-8 carrying the chloroplastic GS2 gene are all co-suppressed for chloroplast GS2 (cf. GS). Controls are: TL—tobacco leaf, PL—pea leaf, and PR—pea root. Total GS activities are shown (as percentages relative to controls=(100%)) below the Western panel. Bottom panel: Coomassie staining of RUBISCO large subunit protein demonstrating approximately equal loading of samples. ctGS-chloroplastic GS2 (~45 kD); cyGS-cytosolic GS (~38 kD).

Figure 6A:
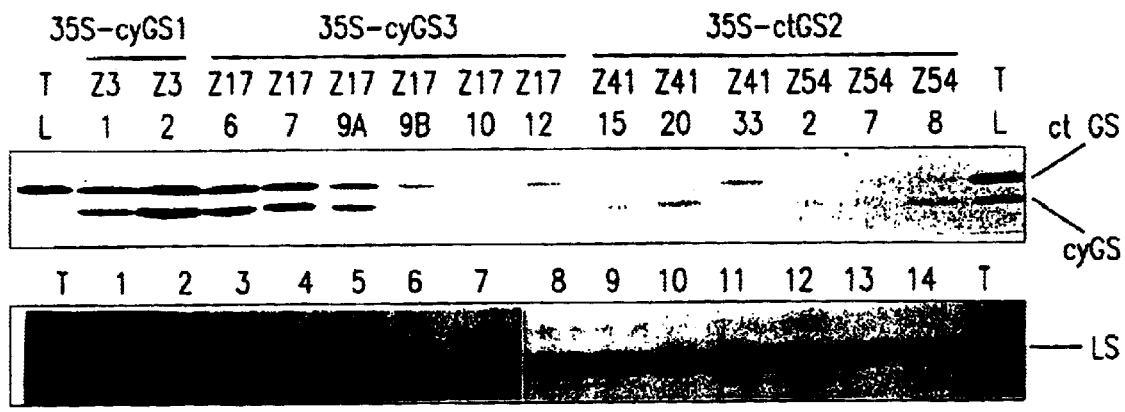
Figure 6B:
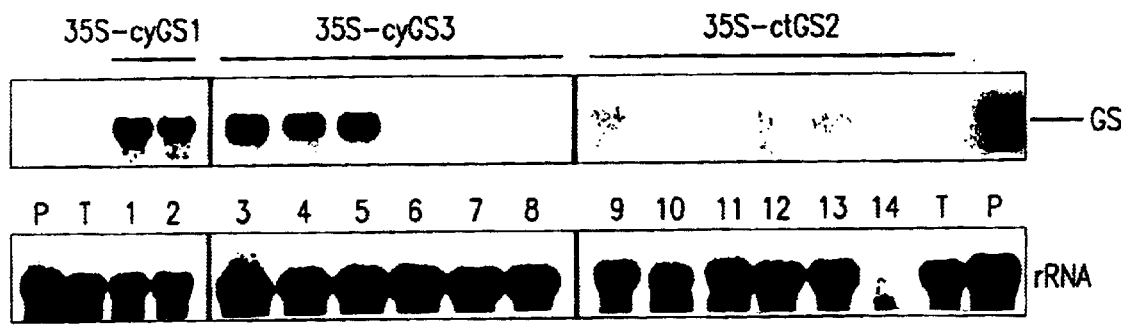
Figure 6C:
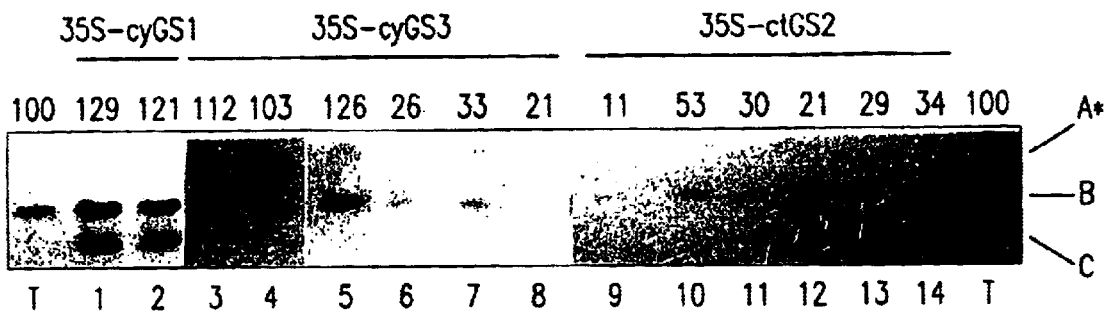

FIG. 6. Analysis of GS Protein, RNA and Holoenzyme from T2 Progeny Transgenic Plants Containing Pea GS Transgenes. Of the four T2 plants from each primary transformant typically analyzed, a single representative plant was included in this figure. In the case of Z17-9, the T2 progenies showed two different profiles and both are shown (Z17-9A and Z17-9B). Controls: TL/T—tobacco leaf, P—pea leaf.

Panel A (upper): Western analysis of GS polypeptides in transgenic plants. Panel A (lower): Coomassie staining of RUBISCO large subunit protein to show approximately equal loading of samples. Panel B (upper): Northern blots hybridized with the approximate cDNA probes for GS1 (left), GS3A (center), and GS2 (right). Panel B (lover): Control hybridization with the pea mRNA gene probe. Panel C: Non-denaturing gel and GS activity analysis showing GS holoenzymes A*, B, and C in transgenic plants. GS activities are expressed as percentages compared to controls (control= 100% activity).

Figure 7A:
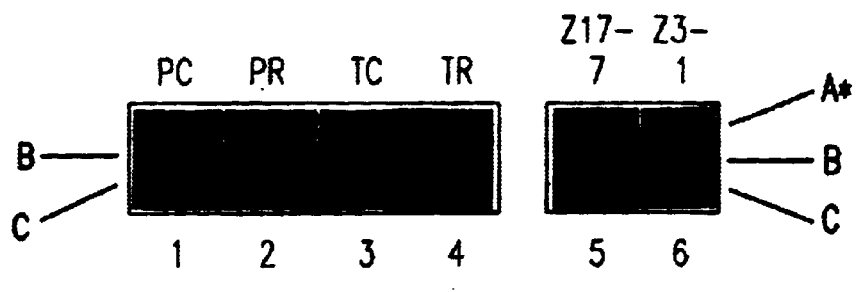

FIG. 7A. Activity Gel Analysis of GS Holoenzymes. Protein extracts from pea chloroplast (PC), pea root (PR), tobacco chloroplast (TC) and tobacco roots (TR) demonstrating the migration of chloroplastic- and cytosolic-enriched GS protein samples relative to the migration of the holoenzymes of GS1 and GS3A overexpressing plants. Lane 1: pea chloroplast protein (PC) has GS holoenzyme B only; lane 2: pea root protein (PR) has GS holoenzyme C only; lane 3: tobacco chloroplast protein (TC) has GS holoenzyme B only; lane 4: tobacco root protein has GS holoenzyme C only. Lane 5: protein from plant Z17-7 (carrying the 35S-GS3A construction) has GS holoenzymes A* and B; lane 5: protein from plant Z3-1 (carrying the 35S-GS1 construction) has GS holoenzymes B and C.

Figure 7B:
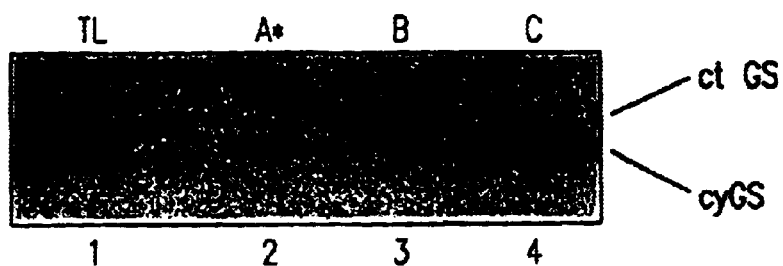

FIG. 7B. Western Analysis of GS Proteins Isolated from GS Holoenzymes A*, B, and C. Holoenzymes A* and C observed in transgenic tobacco overexpressing GS3A and GS1 were excised from non-denaturing gels, re-extracted in protein isolation buffer, and electrophoresed under denaturing conditions for Western analysis using GS antibodies. Lane 1: tobacco leaf protein as control; lane 2: GS holoenzyme A* from Z17-7; lane 3: isolated chloroplast GS2 (holoenzyme B) as control; lane 4: GS holoenzyme C from Z3-1.

Figure 8:
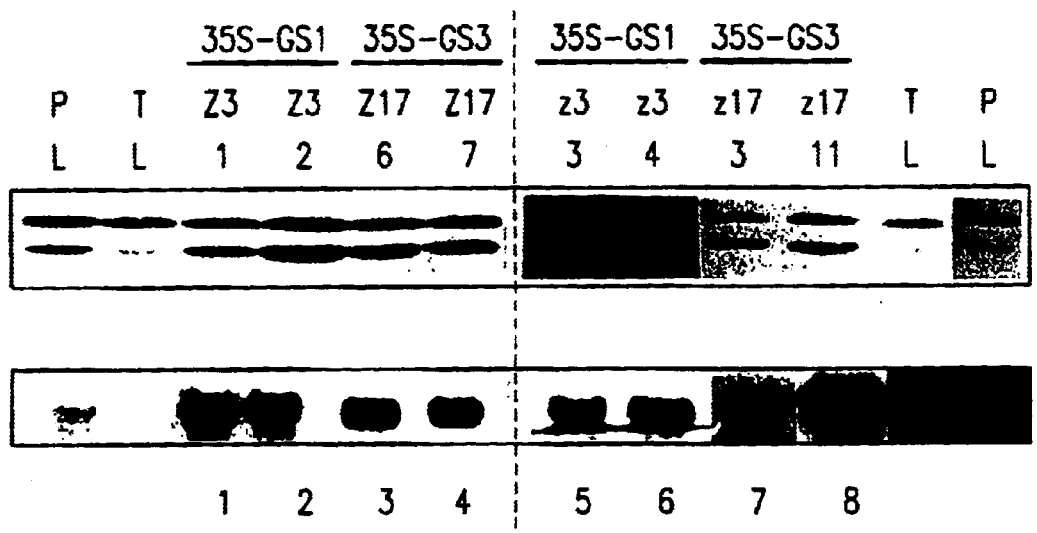

FIG. 8. Western and Northern Analysis of GS Protein and RNA in Transgenic Plants Selected for Growth Analysis Ectopically Expressing either Cytosolic GS1 or GS3A. Upper panel: Western blot for GS proteins. Lower panel: Northern blot for GS mRNA. P1 and T1 are pea and tobacco leaf controls. Lanes 1 and 2, and 5 and 6 are plants overexpressing GS1, and lanes 3 and 4, and 7 and 8 are plants overexpressing GS3A. Transgenic plants to the left of the broken line were analyzed in growth experiment A, and those to the right were analyzed in growth experiment B. Corresponding probes were used in the Northern blot; the left pea control was hybridized to GS1, and the right-hand pea control was hybridized to GS3A.

Figure 9A:
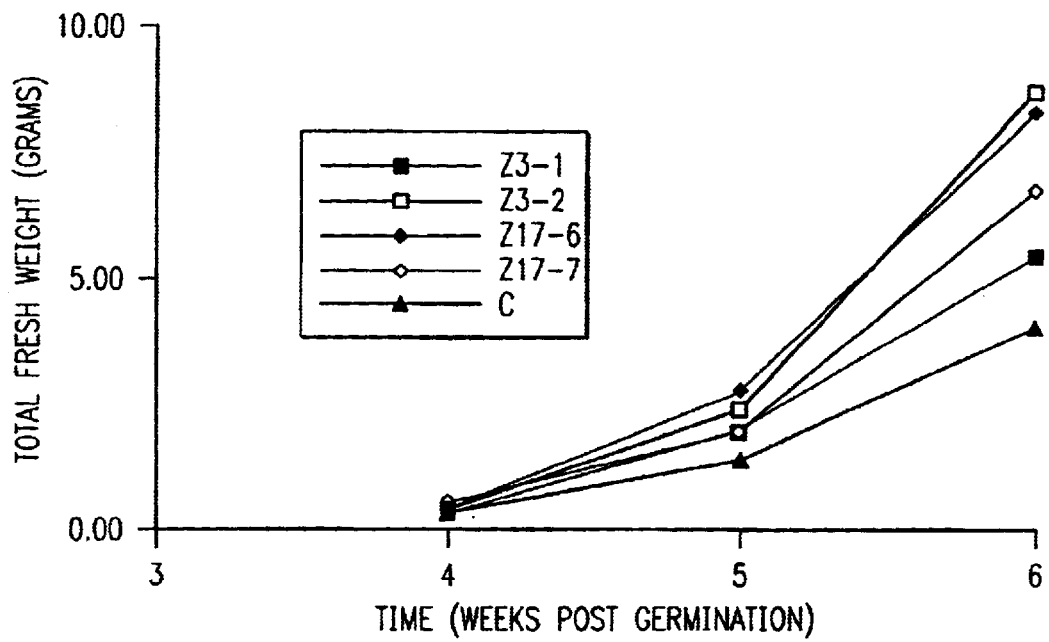
Figure 9B:
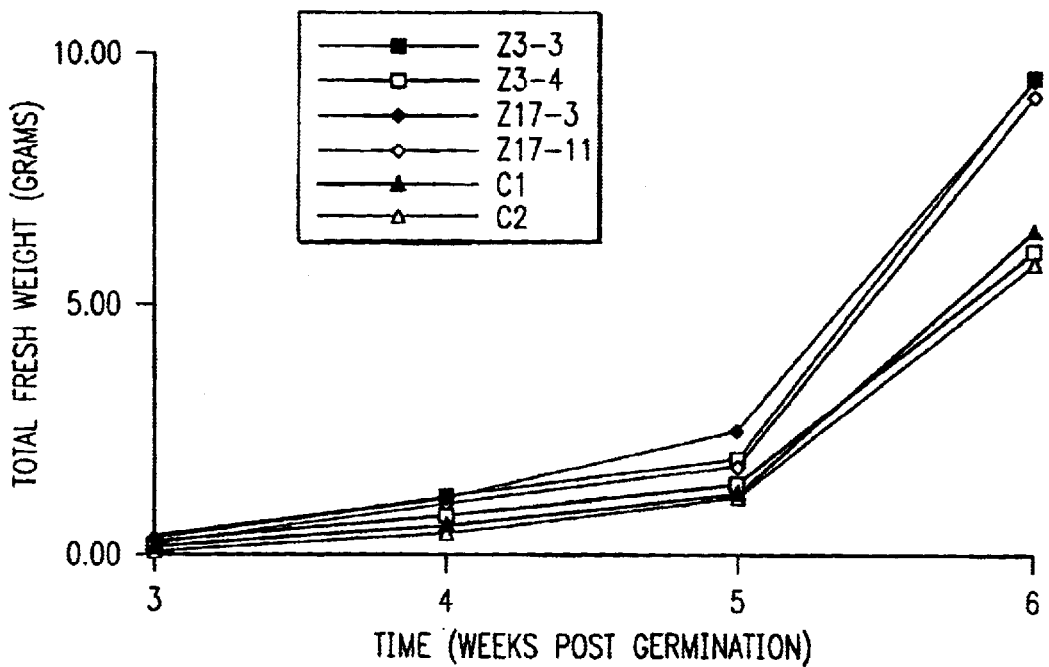

FIG. 9. Increase in fresh weight of transgenic lines overexpressing cytosolic GS1 (Z3) or cytosolic GS3A (Z17). Panel A: The results of experiment A with transgenic lines Z3-1, Z3-2, Z17-6, Z17-7, and a non-transformed control (C). Panel B: The results of experiment B with transgenic lines Z3-3, Z3-4, Z17-3, Z17-11, and two non-transformed controls (C1 and C2). This is a graphic representation of data shown in Table 2, and analyzed statistically in Table 3.

Figure 10:
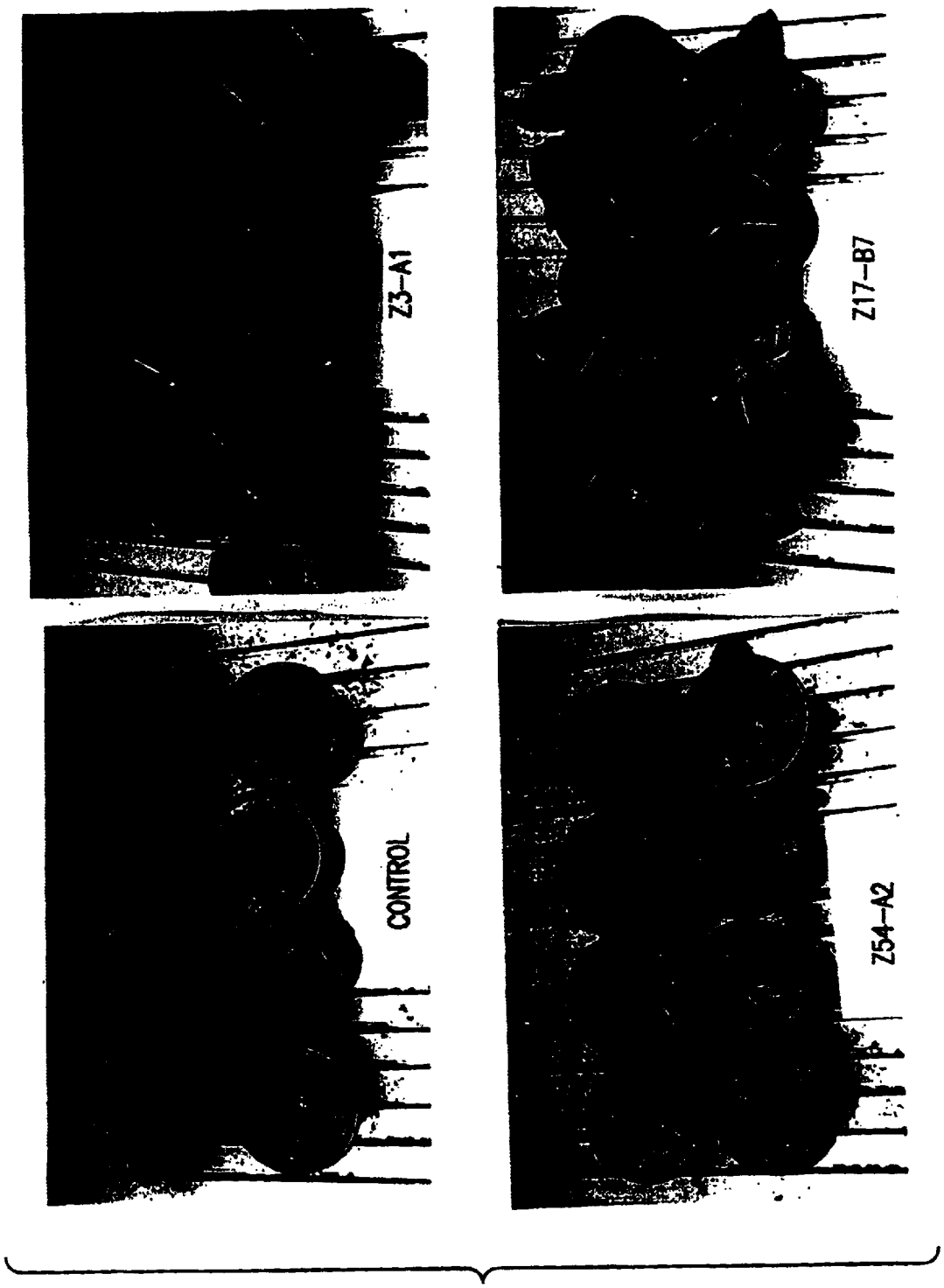

FIG. 10. Qualitative growth pattern of plants with altered GS expression patterns. Plants in each panel were sown at the same time and grown in soil for approximately three weeks. Control panel: SR1 untransformed tobacco (100% GS activity). Z3-A1 panel: Transgenic plants with overexpress GS1 (123% GS activity). Z17-B7 panel: Transgenic plant which overexpresses GS3 (107% GS activity). Z54-A2 Panel; Transgenic plant co-suppressed for GS2 (28% GS activity).

Figure 11A:
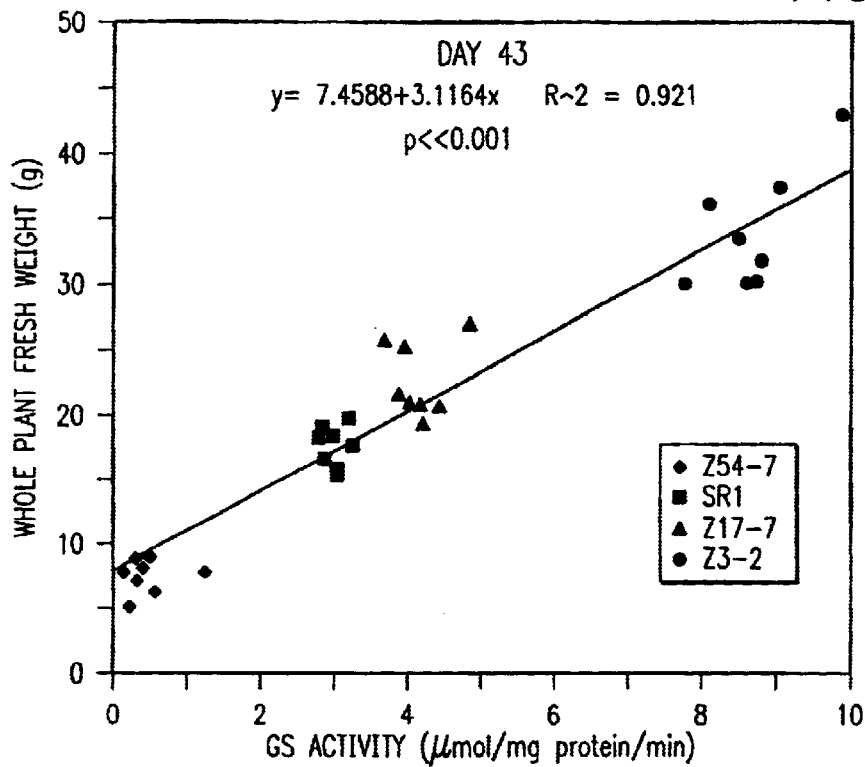
Figure 11B:
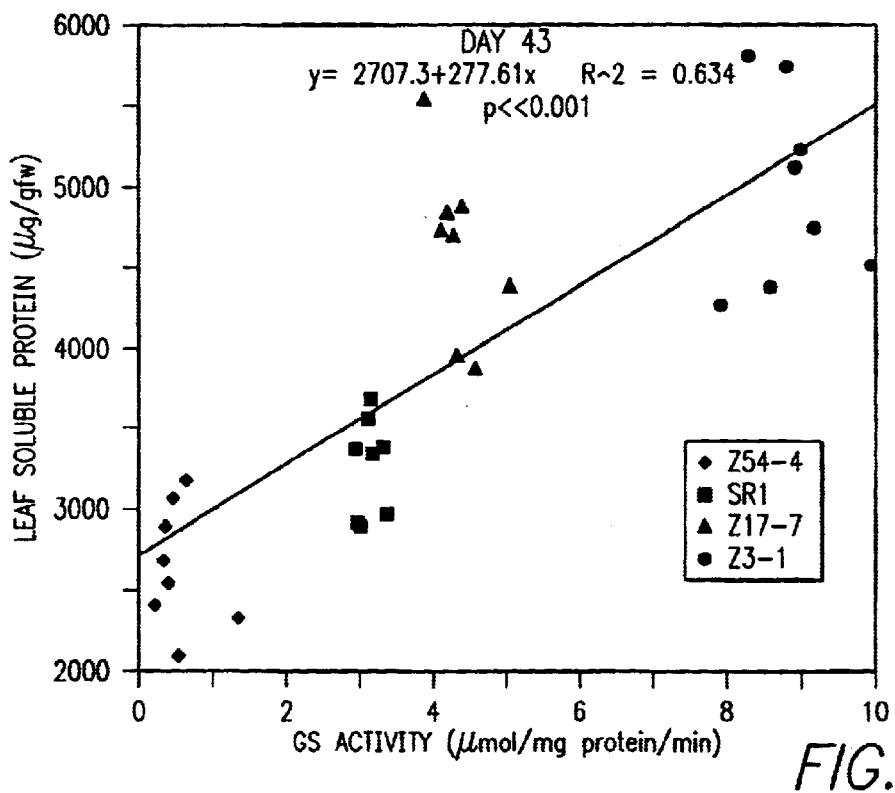

FIGS. 11A and 11B. Linear relationship between GS activity and plant fresh weight or total leaf protein. T2 progenies of primary transformants which showed no segregation of the $Kan^R$ phenotype associated with the transgene were selected for growth analysis. $Kan^R$ T2 plants were selected on MSK media (R. B. Horsch, et al., Science 227:1229 (1985)) and transferred to sand at 18 days. Plants were subirrigated and surface fed every two days with 50 mls of 1×Hoagland's solution (D. R. Hoagland et al., Circ. Calif. Agric. Exp. Stn. 347:461 (1938)) containing 10 mM $KNO_3$. For each line, eight T2 progenies were analyzed individually for total plant fresh weight (grams), specific activity of total leaf GS as determined by the transferase assay (B. M. Shapiro, et al., Methods Enzymol. 17A:910 (1970)) and protein/gram fresh weight. Plants analyzed were: Control, SR1 untransformed tobacco; Z54-4 co-suppressed by GS2; Z17-7 overexpressing GS3A; Z3-1 overexpressing GS1. FIG. 11A; Plant fresh weight vs. GS activity. FIG. 11B; protein/gm fresh weight vs. GS activity.

FIG. 12. Chimeric 35 S CaMV-AS Constructs Transferred to Transgenic tobacco. cDNAs for the AS1 gene and the glnΔAS1 gene were fused to the 35S promoter and nopaline synthase transcriptional terminator for transfer to tobacco using the binary expression vector pTEV5.

FIG. 13. Northern analysis, of transgenic plants expressing either AS1 or glnΔAS1. 10 μg of total RNA isolated from leaves of individual transformants was loaded in leach lane. Blots were probed with the AS1 cDNA from pea. A positive control includes AS mRNA in dark-grown pea leaves (PL). A negative control includes AS mRNA in light-grown tobacco leaves (TL).

FIG. 14. Increase in fresh weight of transgenic lines overexpressing AS1 and glnΔAS1 is expressed graphically from week 3 to week 6 post-germination. This is a graphic representation of data shown in Table (5) and analyzed statistically in Table (6).

5. DETAILED DESCRIPTION OF THE INVENTION

The present invention relates to genetic engineering of nitrogen metabolism in plants. In particular, the invention relates to altering the enzymes involved in nitrogen assimilation or utilization and/or their expression in order to engineer plants with better growth characteristics, enriched nutritional qualities, improved vegetative and yield and/or enhanced seed yield or quality.

Accordingly—without intending to be limited to a particular mechanism—the targets for engineering are genes encoding for enzymes involved in the assimilation of ammonia into the amino acids, glutamine, aspartate, asparagine or glutamate, or in the utilization of these same amino acids in biosynthetic reactions. The target genes include those encoding glutamine synthetase (GS), asparagine synthetase (AS), glutamate 2:oxoglutarate aminotransferase (GOGAT), aspartate aminotransferase (AspAT), glutamate dehydrogenase (GDH) and asparaginase (ANS). See FIG. 1 for a diagram of the roles played by of these enzymes in nitrogen assimilation and utilization.

These enzymes can be altered or their expression can be enhanced, suppressed or otherwise modified (e.g., ectopic expression) to engineer a plant with desirable properties. The engineering is accomplished by transforming plants with nucleic acid constructs described herein. The transformed plants or their progenies are screened for plants that express the desired altered enzyme or exhibit the desired altered expression of the nitrogen assimilation or utilization enzyme, altered expression of the corresponding mRNA, altered nitrogen assimilation or utilization capacities, increased growth rate, enhanced vegetative yield, and/or improved reproductive yields.

Engineered plants exhibiting the desired physiological and/or agronomic changes can be used in plant breeding or directly in agricultural production. These plants having one altered enzyme also may be crossed with other altered plants engineered with alterations in the other nitrogen assimilation or utilization enzymes (e.g., cross a GS overexpressing plant to an AS overexpressing plant) to produce lines with even further enhanced physiological and/or agronomic properties compared to the parents.

The invention is illustrated by working examples of plants engineered for ectopic, overexpression of GS or AS. In all instances, engineered plants that exhibit ectopic, overexpression of GS or AS also show better growth characteristics, enriched nutritional qualities, improved vegetative yield and/or enhanced seed quality or yield over control, wild-type plants.

5.1. Alteration of Nitrogen Assimilatory and Utilization Pathways

In accordance with one aspect of the present invention, desirable plants may be obtained by engineering ectopic overexpression of enzymes involved in initial assimilation of ammonia into amino acids glutamine, asparagine or glutamate and further conversion to aspartate. The term ectopic is used herein to mean abnormal subcellular (e.g., switch between organellar and cytosolic localization), cell-type, tissue-type and/or developmental or temporal expression (e.g., light/dark) patterns for the particular gene or enzyme in question. Such ectopic expression does not necessarily exclude expression in tissues or developmental stages normal for said enzyme but rather entails expression in tissues or developmental stages not normal for the said enzyme. The term overexpression is used herein to mean above the normal expression level in the particular tissue, all and/or developmental or temporal stage for said enzyme.

Key enzymes involved in assimilation of ammonia into glutamine and its further metabolism into glutamate, aspartate, and asparagine are: glutamine synthetase, asparagine synthetase, glutamate 2:oxoglutarate aminotransferase, aspartate aminotransferase, glutamate dehydrogenase and asparaginase. The present invention provides that engineering ectopic overexpression of one or more of these enzymes would produce plants with the desired physiological and agronomic properties. In a preferred embodiment, a plant is engineered for the ectopic overexpression of glutamine synthetase or asparagine synthetase. For GS, where cytosolic and chloroplastic forms of an enzyme exist, engineering of enhanced expression of the cytosolic form is preferred. The cytosolic form of GS includes both nodule-specific (e.g., pea GS3A & B) and root-specific (e.g., pea GS1) enzymes. The engineering of enhanced expression of "root-specific" cytosolic GS (e.g., pea GS1) is especially preferred. The present invention also provides for engineering that alters the subcellular localization of said enzyme. For example, engineering a chloroplast target sequence onto a cytosolic enzyme such as AS, may improve nitrogen assimilation in plants. This would be especially valuable in mesophyll cells to reassimilate photorespiratory ammonia.

In accordance to another aspect of the present invention, desirable plants may be obtained by engineering enhanced ammonia incorporation though an alternate nitrogen assimilation pathway. In particular, the engineering is accomplished by suppressing the normal, major route of nitrogen assimilation through glutamine synthetase. In plant species that encode multiple GS isozymes, this may require the suppression of the endogenous GS genes. In preferred embodiments, a plant engineered with suppressed GS expression is further engineered for ectopic overexpression of an alternative N-assimilatory enzyme such as asparagine synthetase (AS) and/or glutamine dehydrogenase (GDH). In most preferred embodiments, the GS and AS/GDH engineered plant is additionally engineered for enhanced expression of one or more of the other enzymes involved in nitrogen assimilation or utilization processes (see FIG. 1).

In accordance with a third aspect of the present invention, desirable plants may be obtained by engineering ectopic overexpression of an enzyme involved in the utilization of assimilated nitrogen. Embodiments of this aspect of the present invention may involve engineering plants with ectopic overexpression of enzymes catalyzing the use of glutamine, glutamate and asparagine in catabolic reactions. In a preferred embodiment, a plant is engineered for the ectopic overexpression of asparaginase.

In accordance with a fourth aspect of the present invention, desirable plants may be obtained by engineering the expression of an altered, mutated, chimeric, or heterologous form of an enzyme involved in the assimilation or utilization of nitrogen. Embodiments of this aspect of the present invention may involve engineering plants to express nitrogen assimilation or utilization enzymes from a heterologous source (ie. an enzyme from a different plant or organism, including animals and microbes). Additional embodiments may involve developing nitrogen assimilation or utilization enzymes that have increased efficiencies, for example, in substrate binding, catalysis, and/or product release and engineering plants to express such novel enzymes. These novel enzymes may be developed by in vitro mutagenesis of key amino acid residues affecting the aforementioned processes. Alternatively such novel enzymes may be developed by recombining domains from related enzymes. For example, a chimeric bifunctional GOGAT enzyme could be engineered to contain both ferredoxin- and NADH-GOGAT activities by splicing the NADH binding domain of NADH-GOGAT onto the Fd-GOGAT gene (see FIG. 2). Such a chimeric GOGAT enzyme would have the advantage of being able to utilize either NADH or ferredoxin as a reductant in the GOGAT reaction. The ectopic expression of this new enzyme may result in more efficient synthesis of glutamate. Another example of enzyme modification presented herein (see Section 7.0) is the engineering of an AS enzyme which has a domain deleted to alter its substrate specificity.

In accordance to the present invention, controlling the tissue and developmental expression patterns of the nitrogen assimilation or utilization enzymes may be important to achieving the desired plant improvements. In instances where plants are engineered for ectopic overexpression of the enzymes involved in the normal or alternative ammonia assimilation pathways, preferred embodiments of the present invention involve effecting altered expression in many or all parts of the plant. In instances where plants are engineered for ectopic overexpression of enzymes catalyzing the use of assimilated nitrogen, preferred embodiments of the present invention limit such expressions to nitrogen "sink" tissues and structures such as leaves and seeds.

5.2. Generating Transgenic Plants
5.2.1. Nucleic Acid Constructs

The properties of the nucleic acid sequences are varied as are the genetic structures of various potential host plant cells. The preferred embodiments of the present invention will describe a number of features which an artisan may recognize as not being absolutely essential, but clearly advantageous. These include methods of isolation, synthesis or construction of gene constructs, the manipulations of the gene constructs to be introduced into plant cells, certain features of the gene constructs, and certain features of the vectors associated with the gene constructs.

Further, the gene constructs of the present invention may be encoded on DNA or RNA molecules. According to the present invention, it is preferred that the desired, stable genotypic change of the target plant be effected through genomic integration of exogenously introduced nucleic acid construct(s), particularly recombinant DNA constructs. Nonetheless, according to the present inventions, such genotypic changes can also be effected by the introduction of episomes (DNA or RNA) that can replicate autonomously and that are somatically and germinally stable. Where the introduced nucleic acid constructs comprise RNA, plant transformation or gene expression from such constructs may proceed through a DNA intermediate produced by reverse transcription.

The nucleic acid constructs described herein can be produced using methods well known to those skilled in the art. Artisans can refer to sources like Sambrook et al., 1989, *Molecular Cloning: a laboratory manual*, Cold Spring Harbor Laboratory Press, Plainview, N.Y. for teachings of recombinant DNA methods that can be used to isolate, characterize, and manipulate the components of the constructs as well as to built the constructs themselves. In some instances, where the nucleic acid sequence of a desired component is known, it may be advantageous to synthesize it rather than isolating it from a biological source. In such instances, an artisan can refer to teachings of the likes of Caruthers et al., 1980, Nuc. Acids Res. Symp. Ser. 7:215–233, and of Chow and Kempe, 1981, Nuc. Acids Res. 9:2807–2817. In other instances, the desired components may be advantageously produced by polymerase chain reaction (PCR) amplification. For PCR teachings, an artisan can refer to the like of Gelfand, 1989, *PCR Technology, Principles and Applications for DNA Amplification*, H. A. Erlich, ed., Stockton Press, N.Y., *Current Protocols In Molecular Biology*, Vol. 2, Ch. 15, Ausubel et al. eds., John Wiley & Sons, 1988.

5.2.1.1. Expression Constructs

In accordance to the present invention, a plant with ectopic overexpression of a nitrogen assimilation or utilization enzyme may be engineered by transforming a plant cell with a gene construct comprising a plant promoter operably associated with a sequence encoding the desired enzyme. (Operably associated is used herein to mean that transcription controlled by the "associated" promoter would produce a functional messenger RNA, whose translation would produce the enzyme.) In a preferred embodiment of the present invention, the associated promoter is a strong and non tissue- or developmental-specific plant promoter (e.g. a promoter that strongly expresses in many or all tissue types). Examples of such strong, "constitutive" promoters include, but are not limited to, the CaMV 35S promoter, the T-DNA mannopine synthetase promoter, and their various derivatives.

In another embodiment of the present invention, it may be advantageous to engineer a plant with a gene construct operably associating a tissue- or developmental-specific promoter with a sequence encoding the desired enzyme. For example, where expression in photosynthetic tissues and organs are desired, promoters such as those of the ribulose bisphosphate carboxylase (RUBISCO) genes or chlorophyll a/b binding protein (CAB) genes may be used; where expression in seed is desired, promoters such as those of the various seed storage protein genes may be used; where expression in nitrogen fixing nodules is desired, promoters such those of the legehemoglobin or nodulin genes may be used; where root specific expression is desired, promoters such as those encoding for root-specific glutamine synthetase genes may be used (see Tingey et al., 1987, EMBO J. 6:1–9; Edwards et al., 1990, Proc. Nat. Acad. Sci. USA 87:3459–3463).

In an additional embodiment of the present invention, it may be advantageous to transform a plant with a gene construct operably associating an inducible promoter with a sequence encoding the desired enzyme. Examples of such promoters are many and varied. They include, but are not limited to, those of the heat shock genes, the defense responsive gene (e.g., phenylalanine ammonia lyase genes), wound induced genes (e.g., hydroxyproline rich cell wall protein genes), chemically-inducible genes (e.g., nitrate reductase genes, gluconase genes, chitinase genes, etc.), dark-inducible genes (e.g., asparagine synthetase gene (Coruzzi and Tsai, U.S. Pat. No. 5,256,558, Oct. 26, 1993, Gene Encoding Plant Asparagine Synthetase) to name just a few.

In yet another embodiment of the present invention, it may be advantageous to transform a plant with a gene construct operably linking a modified or artificial promoter to a sequence encoding the desired enzyme. Typically, such promoters, constructed by recombining structural elements of different promoters, have unique expression patterns and/or levels not found in natural promoters. See e.g., Salina et al., 1992, Plant Cell 4:1485–1493, for examples of artificial promoters constructed from combining cis-regulatory elements with a promoter core.

In yet an additional embodiment of the present invention, the ectopic overexpression of a nitrogen assimilation or utilization enzyme may be engineered by increasing the copy number of the gene encoding the desired enzyme. One approach to producing a plant cell with increased copies of the desired gene is to transform with nucleic acid constructs that contain multiple copies of the gene. Alternatively, a gene encoding the desired enzyme can be placed in a nucleic acid construct containing an amplification-selectable marker (ASM) gene such as the glutamine synthetase or dihydrofolate reductase gene. Cells transformed with such constructs is subjected to culturing regimes that select cell lines with increased copies of ASK gene. See Donn et al., 1984, J. Mol. Appl. Genet. 2:549–562, for a selection protocol used to isolate of a plant cell line containing amplified copies of the GS gene. Because the desired gene is closely linked to the ASH gene, cell lines that amplified the ASH gene would also likely to have amplified the gene encoding the desired enzyme.

In one more embodiment of the present invention, the ectopic overexpression of a nitrogen assimilation or utilization enzyme may be engineered by transforming a plant cell with nucleic acid construct encoding a regulatory gene that controls the expression of the endogenous gene or an transgene encoding the desired enzyme, wherein the introduced regulatory gene is modified to allow for strong expression of the enzyme in the desired tissues and/or developmental stages. synthetase promoter, and their various derivatives.

5.2.1.2 Suppression Constructs

In accordance to the present invention, a desired plant may be engineered by suppressing GS activity or the activities of other enzymes in nitrogen assimilation/metabolism (FIG. 1). In an embodiment, the suppression may be engineered by transforming a plant cell with a gene construct encoding an antisense RNA complementary to a segment or the whole of a host target RNA transcript, including the mature target mRNA. In another embodiment, target gene (e.g., GS mRNA) suppression may be engineered by transforming a plant cell with a gene construct encoding a ribozyme that cleaves a host target RNA transcript, (e.g., GS RNA transcript, including the mature GS mRNA).

In yet another embodiment, target gene suppression may be engineered by transforming a plant cell with a gene construct encoding the target enzyme containing a "dominant negative" mutation. Preferred mutations are those affecting catalysis, substrate binding (e.g., for GS, the binding site of glutamate or ammonium ion), or product release. A useful mutation may be a deletion or point-mutation of the critical residue(s) involved with the above-mentioned processes. An artisan can refer to teachings herein and of Herskowitz (Nature, 329:219–222, 1987) for approaches and strategies to constructing dominant negative mutations.

For all of the aforementioned suppression constructs, it is preferred that such gene constructs express with the same tissue and developmental specificity as the target gene. Thus, it is preferred that these suppression constructs be operatively associated with the promoter of the target gene. Alternatively, it may be preferred to have the suppression constructs expressed constitutively. Thus, a strong, constitute promoter, such as the CaMV 35S promoter, may also be used to express the suppression constructs. A most preferred promoter for these suppression constructs is a modified promoter of the target gene, wherein the modification results in enhanced expression of the target gene promoter without changes in the tissue or developmental specificities.

In accordance with the present invention, desired plants with suppressed target gene expression may also be engineered by transforming a plant cell with a co-suppression construct. A co-suppression construct comprises a functional promoter operatively associated with a complete or partial coding sequence of the target gene. It is preferred that the operatively associated promoter be a strong, constitutive promoter, such as the CaMV 35S promoter. Alternatively, the co-suppression construct promoter can be one that expresses with the same tissue and developmental specificity as the target gene. Such alternative promoters could include the promoter of the target gene itself (e.g., a GS promoter to drive the expression of a GS co-suppression construct).

According to the present invention, it is preferred that the co-suppression construct encodes a incomplete target mRNA or defective target enzyme, although a construct encoding a fully functional target RNA or enzyme may also be useful in effecting co-suppression.

In embodiments, where suppression of most, if not all, GS isozymes is desired, it is preferred that the co-suppression construct encodes a complete or partial copy of chloroplastic GS mRNA (e.g., pea GS2 mRNA). As disclosed herein (section 6.2.2.), such constructs are particularly effective in suppressing the expression of the target gene.

In accordance with the present invention, desired plants with suppressed target gene expression may also be engineered by transforming a plant cell with a construct that can effect site-directed mutagenesis of the endogenous target gene. (See Offringa et al., 1990, EMBO J. 9:3077–84; and Kanevskii et al., 1990, Dokl. Akad. Nauk. SSSR 312:1505–1507) for discussions of nucleic constructs for effecting site-directed mutagenesis of target genes in plants.) It is preferred that such constructs effect suppression of target gene by replacing the endogenous target gene sequence through homologous recombination with none or inactive coding sequence.

5.2.1.3. Other Features of Recombinant Nucleic Acid Constructs

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding β-glucuronidase (Jefferson, 1987, Plant Molec Biol. Rep 5:387–405), luciferase (Ow et al., 1986, Science 234:856–859), B and C1 gene products that regulate anthocyanin pigment production (Goff et al., 1990, EMBO J 9:2517–2522).

In embodiments of the present invention which utilize the Agrobacterium system for transforming plants (see infra), the recombinant DNA constructs additionally comprise at least the right T-DNA border sequence flanking the DNA sequences to be transformed into plant cell. In preferred embodiments, the sequences to be transferred in flanked by the right and left T-DNA border sequences. The proper design and construction of such T-DNA based transformation vectors are well known to those skilled in the art.

5.2.2. Transformation of Plants and Plant Cells

According to the present invention, a desirable plant may be obtained by transforming a plant cell with the nucleic acid constructs described herein. In some instances, it may be desirable to engineer a plant or plant cell with several different gene constructs. Such engineering nay be accomplished by transforming a plant or plant cell with all of the desired gene constructs simultaneously. Alternatively, the engineering may be carried out sequentially. That is, transforming with one gene construct, obtaining the desired transformant after selection and screening, transforming the transformant with a second gene construct, and so on. In preferred embodiments each gene constructs would be linked to a different selectable or screenable marker gene so as to facilitate the identification of plant transformants containing multiple gene inserts. In another embodiment, several different genes may be incorporated into one plant by crossing parental lines engineered for each gene.

In an embodiment of the present invention, Agrobacterium is employed to introduce the gene constructs into plants. Such transformations preferably use binary Agrobacterium T-DNA vectors (Bevan, 1984, Nuc. Acid Res. 12:8711–8721), and the co-cultivation procedure (Horsch et al., 1985, Science 227:1229–1231). Generally, the Agrobacterium transformation system is used to engineer dicotyledonous plants (Bevan et al., 1982, Ann. Rev. Genet 16:357–384; Rogers et al., 1986, Methods Enzymol. 118:627–641). The Agrobacterium transformation system may also be used to transform as well as transfer DNA to monocotyledonous plants and plant cells. (see Hernalsteen et al., 1984, EMBO J 3:3039–3041; Hooykass-Van Slogteren et al., 1984, Nature 311:763–764; Grimsley et al., 1987, Nature 325:1677–179; Boulton et al., 1989, Plant Mol. Biol. 12:31–40.; Gould et al., 1991, Plant Physiol. 95:426–434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, protoplast transformation through calcium-, polyethylene glycol (PEG)- or electroporation-mediated uptake of naked DNA (see Paszkowski et al., 1984, EMBO J 3:2717–2722, Potrykus et al. 1985, Molec. Gen. Genet. 199:169–177; Fromm et al., 1985, Proc. Nat. Acad. Sci. USA 82:5824–5828; Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Nat. Acad. Sci. USA 85:4305–4309; Gordon-Kamm et al., 1990, Plant Cell 2:603–618).

According to the present invention, a wide variety of plants and plant cell systems may be engineered for the desired physiological and agronomic characteristics described herein using the nucleic acid constructs of the instant invention and the various transformation methods mentioned above. In preferred embodiments, target plants and plant cells for engineering include, but are not limited to, those of maize, wheat, rice, soybean, tomato, tobacco, carrots, potato, sugar beets, sunflower, yam, Arabidopsis, rape seed, and petunia.

5.2.3. Selection and Identification of Transformed Plants and Plant Cells

According to the present invention, desired plants may be obtained by engineering the disclosed gene constructs into a variety of plant cell types, including but not limited to, protoplasts, tissue culture cells, tissue and organ explants, pollens, embryos as well as whole plants. In an embodiment of the present invention, the engineered plant material is selected or screened for transformants (those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be also to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, inmunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

5.2.4. Screening of Transformed Plants for Those With Improved Agronomic Traits

According to the present invention, to obtain plants with improved agronomic characteristics, the transformed plants may be screened for those exhibiting the desired physiological alteration. For example, where the plants have been engineered for ectopic overexpression of a GS enzyme, transformed plants are examined for those expressing the GS enzyme at the desired level and in the desired tissues and developmental stages. Where the plants have been engineered for suppression of a target gene, transformed plants are examined for those expressing the target gene product (e.g., RNA or protein) at reduced levels in various tissues. The plants exhibiting the desired. physiological changes, e.g., ectopic GS overexpression or GS suppression, may then be subsequently screened for those plants that have the desired agronomic changes.

Alternatively, the transformed plants may be directly screened for those exhibiting the desired agronomic changes. In one embodiment, such screening may be for productive growth of the transformed plants under nitrogen nutrient deficient conditions. That is screen for growth of transformed plants under conditions, with respect to the available nitrogen nutrient, that cause the growth of wild-type plant to cease or to be so diminished as to significantly reduce the size or quality of the wild-type plant. An example of a nitrogen nutrient deficient condition for tobacco and plants with similar nitrogen nutrient requirements is that where the sole nitrogen nutrient in the soil or synthetic medium is (a) nitrate supplied or periodically applied at a concentration of 0.5 mM or lower, or (b) physiological equivalents of nitrate (e.g., ammonium or a mix of nitrate and ammonium) supplied or periodically applied at a concentration that is physiologically equivalent to 0.5 mM nitrate or lower (see Eckes et al., 1988, Australian Patent Office document no. AU-A-17321/88). Another example of a nitrogen nutrient deficient condition is that where the steady state level of the available nitrogen nutrient in the soil or synthetic medium is less than about 0.02 mM nitrate or physiological equivalents thereof. The term nitrate as used herein means any one or any mix of the nitrate salts commonly used as plant nitrogen fertilizer, e.g., potassium nitrate, calcium nitrate, sodium nitrate, ammonium nitrate, etc. The term ammonium as used herein means any one or any mix of the ammonium salts commonly used as plant nitrogen fertilizer, e.g., ammonium nitrate, ammonium chloride, ammonium sulfate, etc.

In other embodiments, the screening of the transformed plants may be for improved agronomic characteristics (e.g., faster growth, greater vegetative or reproductive yields, or improved protein contents, etc.), as compared to unengineered progenitor plants, when cultivated under nitrogen non-limiting growth conditions (i.e., cultivated using soils or media containing or receiving sufficient amounts of nitrogen nutrients to sustain healthy plant growth). An example of nitrogen non-limiting conditions for tobacco and plants with similar nitrogen nutrient requirements is that where the sole nitrogen nutrient in soil or synthetic medium is (a) nitrate supplied or periodically applied at a concentration of 10 mM or higher, or (b) physiological equivalents of nitrate supplied or periodically applied at a concentration that is physiologically equivalent to 10 mM nitrate or higher. Another example of nitrogen non-limiting conditions is that where the steady state level of the available nitrogen nutrient in the soil or synthetic medium is at least about 1.0 mM potassium nitrate or physiological equivalents thereof. Additional guidance with respect to what are nitrogen nutrient deficient or "non-limiting" conditions for plant growth may be found in the art. See for example, Hewitt, E. J., *Sand and Water Culture Methods Used in the Study of Plant Nutrition*, 2nd ed., Farnham Royal (Bucks), Commonwealth Agricultural Bureaux, 1966; and Hewitt, E. J., *Plant Mineral Nutrition*, London, English University. Press, 1975.

In embodiments where the transformed plants are legumes, direct screenings for transformed plants with the desired agronomic changes and improvements may be conducted as described above but under conditions where nodule formation or nitrogen-fixation is suppressed.

According to the present invention, plants engineered with the alterations in nitrogen assimilation or utilization processes may exhibit improved nitrogen contents, altered amino acid or protein compositions, vigorous growth characteristics, increased vegetative yields or better seed yields and qualities. Engineered plants and plant lines possessing such improved agronomic characteristics may be identified by examining any of following parameters: 1) the rate of growth, measured in, terms of rate of increase in fresh or dry weight; 2) vegetative yield of the mature plant, in terms of fresh or dry weight; 3) the seed or fruit yield; 4) the seed or fruit weight; 5) the total nitrogen content of the plant; 6) the total nitrogen content of the fruit or seed; 7) the free amino acid content of the plant; 8) the free amino acid content of the fruit or seed; 9) the total protein content of the plant; and 10) the total protein content of the fruit or seed. The procedures and methods for examining these parameters are well known to those skilled in the art.

According to the present invention, a desired plant is one that exhibits improvement over the control plant (i.e., progenitor plant) in one or more of the aforementioned parameters. In an embodiment, a desired plant is one that shows at least 5% increase over the control plant in at least one parameter. In a preferred embodiment, a desired plant is one that shows at least 20% increase over the control plant in at least one parameter. Most preferred is a plant that shows at least 50% increase in at least one parameter.

5.3. Utility of the Invention

The engineered plants of the present invention may be productively cultivated under nitrogen nutrient deficient conditions (i.e., nitrogen-poor soils and low all nitrogen fertilizer inputs) that would cause the growth of wild-type plants to cease or to be so diminished as to make the wild-type plants practically useless. The engineered plants also may be advantageously used to achieve earlier maturing, faster growing, and/or higher yielding crops and/or produce more nutritious foods and animal feedstocks when cultivated using nitrogen non-limiting growth conditions (i.e., soils or media containing or receiving sufficient amounts of nitrogen nutrients to sustain healthy plant growth). Nitrogen non-limiting growth conditions vary between species and for varieties within a species. However, one skilled in the art knows what constitute nitrogen non-limiting growth conditions for the cultivation of most, if not all, important crop and ornamental plants. For example, for the cultivation of wheat see Alcoz et al., Agronomy Journal 85:1198–1203 (1993), Rao and Dao, J. Am. Soc. Agronomy 84:1028–1032 (1992), Howard and Lessman, Agronomy Journal 83:208–211 (1991); for the cultivation of corn see Tollenear et al., Agronomy Journal 85:251–255 (1993), Straw et al., Tennessee Farm and Home Science: Progress Report, 166:20–24 (Spring 1993), Miles, S. R., J. Am. Soc. Agronomy 26:129–137 (1934), Dara et al., J. Am. Soc. Agronomy 84:1006–1010 (1992), Binford et al., Agronomy Journal 84:53–59 (1992); for the cultivation of soybean see Chen, et al., Canadian Journal of Plant Science 72:1049–1056 (1992), Wallace et al. Journal of Plant Nutrition 13:1523–1537 (1990); for the cultivation of rice see Oritani and Yoshida, Japanese Journal of Crop Science 53:204–212 (1984); for the cultivation of linseed see Diepenbrock and Porksen, Industrial Crops and Products 1:165–173 (1992); for the cultivation of tomato see Grubinger et al., Journal of the American Society for Horticultural Science 118:212–216 (1993), Cerne, M., Acta Horticulture 277:179–182, (1990); for the cultivation of pineapple see Magistad et al. J. Am. Soc. Agronomy 20 24:610–622 (1932), Asoegwu, S. N., Fertilizer Research 15:203–210 (1988), Asoegwu, S. N., Fruits 42:505–509 (1987), for the cultivation of lettuce see Richardson and Hardgrave, Journal of the Science of Food and Agriculture 59:345–349 (1992); for the cultivation of mint see Munsi, P. S., Acta Horticulturae 306:436–443 (1992); for the cultivation of camomile see Letchamo, W., Acta Horticulturae 306:375–384 (1992); for the cultivation of tobacco see Sisson et al., Crop Science 31:1615–1620 (1991); for the cultivation of potato see Porter and Sisson, American Potato Journal, 68:493–505 (1991); for the cultivation of brassica crops see Rahn et al., Conference "Proceedings, second congress of the European Society for Agronomy" Warwick Univ., p.424–425 (Aug. 23–28, 1992); for the cultivation of banana see Hegde and Srinivas, Tropical Agriculture 68:331–334 (1991), Langenegger and Smith, Fruits 43:639–643 (1988); for the cultivation of strawberries see Human and Kotze, Communications in Soil Science and Plant Analysis 21:771–782 (1990); for the cultivation of songhum see Mahalle and Seth, Indian Journal of Agricultural Sciences 59:395–397 (1989); for the cultivation of plantain see Anjorin and Obigbesan, Conference "International Cooperation for Effective Plantain and Banana Research" Proceedings of the third meeting. Abidjan, Ivory Coast, p. 115–117 (May 27–31, 1985); for the cultivation of sugar cane see Yadav, R. L., Fertiliser News 31:17–22 (1986), Yadav and Sharma, Indian Journal of Agricultural Sciences 53:38–43 (1983); for the cultivation of sugar beet see Draycott et al., Conference "Symposium Nitrogen and Sugar Beet" International Institute for Sugar Beet Research—Brussels Belgium, p. 293–303 (1983). See also Goh and Haynes, "Nitrogen and Agronomic Practice" in *Mineral Nitrogen in the Plant-Soil System*, Academic Press, Inc., Orlando, Fla., p. 379–468 (1986), Engelstad, O. P., *Fertilizer Technology and Use*, Third Edition, Soil Science Society of America, p.633 (1985), Yadav and Sharmna, Indian Journal of Agricultural Sciences, 53:3–43 (1983).

GS suppression have utility in that some GS suppressed plants, particularly legumes, may grow faster or have higher nitrogen contents than non-suppressed plants. (See Knight and Langston-Unkefer, Science 241:951–954). GS suppressed plants may also have altered amino acid or protein contents, making such plants useful in preparation of special dietary foods. Further, all the engineered plants disclosed herein may also serve as breeding stocks for developing agriculturally useful plant lines.

6. EXAMPLE

Ectopic Overexpression of Glutamine Synthetase in Plants Causes an Increase in Plant Growth Phenotype Described herein is a molecular-genetic approach to manipulate nitrogen use efficiency in transgenic plants. The approach relies on the ectopic expression of glutamine synthetase, that express GS in cell-types and/or at levels which the GS expression is not normally found. The pattern of cell-specific GS expression in transgenic plants is altered by constitutively overexpressing the cytosolic GS (which is normally only expressed in phloem) in all cell-types. Such ectopic expression of GS may circumvent physiological limitations which result from the compartmentalization and cell-type specificity of nitrogen assimilatory enzymes. The ectopic high-level expression of cytosolic GS in mesophyll cells might provide an alternate route for the reassimilation of ammonia lost via photorespiration. This may provide a growth advantage as the amount of ammonia lost via photorespiration exceeds primary nitrogen assimilation by 10-fold (Wallsgrove et al., 1983, Plant Cell Environ. 6:301–309; Keys et al., 1978, Nature, 275:741–743). The studies disclosed herein show that constitutive overexpression of a heterologous GS subunit for cytosolic GS leads to increases in GS mRNA, GS protein, total GS activity, native GS holoenzyme, and, in one case, to the production of a novel GS holoenzyme. Transformed plants which overexpress cytosolic GS have a statistically significant growth advantage compared to wild type. They grow faster, attain a higher final fresh weight and have more soluble proteins than untransformed progenitor plants during the vegetative stage of their development. In some instances, however, overexpression of cytosolic GS and/or chloroplastic GS leads to a down regulation of endogenous gene expression or co-suppression. Some transformed plants containing cytosolic GS overexpression constructs and all transformed plants containing chloroplastic GS2 constructs do not overexpress GS, but rather are suppressed for GS expression, including suppression of the endogenous GS gene (i.e., co-suppression). Such GS co-suppressed plants may show poorer growth characteristics, but may have altered amino acid and protein contents due to shunting of nitrogen into other nitrogen assimilation/metabolism pathways.

6.1. Material and Methods
6.1.1. Plant Expression Vector Construction

Plant expression vectors pTEV 4,5,7, and 8 were constructed as follows. A HindIII-EcoRI fragment containing the 35S promoter from the Strasbourg strain of the Cauliflower mosaic virus (CaMV) extending from −941 to +26 relative to the start of transcription was inserted into pBluescript KS II-(pT109) (Hohn et al., 1982, Curr. Topics Microbiol. Immunol. 96:194–236). The polylinker sequence between the HindIII and XhoI sites was then modified to include XbaI, SstI, and StuI sites (pT145). This enabled a T4 polymerase-treated SstI-EcoRI fragment derived from pBIN19 (Clontech) and containing the nopaline synthase transcriptional terminator to be inserted at the StuI site creating pT161. The expression cassette thus constructed was flanked by EcoRI sites and was transferred to pW3, a plasmid derived from pBIN19 (Bevan, 1984, Nucleic Acids Res. 12:8711–8721) containing a modified polylinker. A clone oriented with the 5' end of the promoter adjacent to the left border of pW3 was selected (pW63) and numerous cloning sites were inserted between promoter and terminator. This created the following binary vectors with the unique cloning sites listed (FIG. 3): pTEV4 (HindIII-XbaI-BamHI-XhoI), pTEV5 (HindIII-StuI-SstI-KpnI), pTEV8 (HindIII-XhoI-BamHI-XbaI), pTEV9 (HindIII-KpnI-SstI-StuI).

6.1.2. Transfer of GS cDNAs to Binary Expression Vectors cDNAs corresponding to the pea genes for cytosolic GS1 and GS3A, and chloroplastic GS2 were transferred from pBluescript to the binary expression vectors described above (see FIG. 4). These cDNAs have previously been described as GS299, GS341, and GS185 respectively (Tingey et al., 1987, EMBO J. 6:1–9; Tingey et al., 1988, J. Biol. Chem. 263:9651:9657). For chloroplastic GS2, a modified cDNA was constructed which incorporated the first intron of the genomic sequence into the cDNA at the appropriate position (Z54). This was made using the polymerase chain reaction to amplify a fragment extending from the 5' end of the cDNA to the BsmI site located within exon 2 (at amino acid 43), which could then be cloned into the cDNA in pBluescript. For cytosolic GS3A a modified cDNA (Z17) was constructed by exchange-cloning a BglII-KpnI fragment from a genomic GS3A clone into the pBluescript cDNA clone generating a cDNA sequence into which all genomic introns (from amino acid 6 onwards) had been inserted. The purpose of constructing cDNA incorporating introns was to attempt to enhance expression in transgenic plants as has been shown in monocots (Sinibaldi and Mettler, 1991). The cDNAs were transferred from pBluescript to the following binary expression vectors: GS1—pTEV4 into XbaI-XhoI sites to four pZ3 (NRRL Accession No. B-21330); GS3A and modified GS3A—pTEV4 into XbaI-XhoI sites to form, respectively, pZ9 (NRRL Accession No. B-21331) and pZ17 (NRRL Accession No. 21332); GS2 and modified GS2—pTEV5 into StuI-KpnI sites to form respectively, pZ41 (NRRL Accession No. B-21333) and pZ54 (NRRL Accession No. B-31334).

6.1.3. Plant Transformations

Binary vector constructions were transferred into the disarmed Agrobacterium strain LBA4404 by triparental mating using a previously described procedure (Bevan, 1984, Nucleic Acids Res. 12:8711–8721). Nicotiana tabacum line SRI was transformed by a leaf inoculation procedure (Horsch et al., 1985, Science 227–1299–1231), and regenerated shoots were selected on medium containing 200 μg/ml kanamycin. Primary transformants were maintained in sterile culture and subsequently grown to maturity in soil. Transgenic seeds were sterilized in 10% sodium hypochlorite and germinated on medium containing 100 μg/ml kanamycin.

6.1.4. GS Protein and Enzyme Activity Analysis

Soluble proteins were extracted from tobacco and pea leaf tissue as previously described (Tingey and Coruzzi, 1987, Plant Physiol. 84:366–373). Proteins were denatured and separated in 12% acrylamide by SDS-PAGE and electroblotted onto nitrocellulose. Western analysis was undertaken using the ProtoBlot kit supplied by Promega and a mixture of antibodies raised to tobacco chloroplast GS2 and Phaseolus cytosolic GS (Hirel et al., 1984, Plant Physiol. 74:448–450; Lara et al., 1984, Plant Physiol. 76:1019–1023). Total GS activity in transformants was determined using a previously described ADP-dependent transferase assay (Shapiro and Stadtman, 1970, Methods Enzymol. 17A;910–922). Non-denaturing gel electrophoresis followed a published protocol (Davis, 1964, Annals New York Acad. Sci. 121:404–427) in conjunction with the ADP-dependent transferase assay for GS isozyme detection.

6.1.5. RNA Analysis

RNA was isolated using "RNA matrix" from Bio101 following the protocol suggested by the manufacturer. Total RNA was electrophoresed in 40 mM triethanolamine, 2 mM EDTA and 3.2% formaldehyde in 1.2% agarose (Thomas, 1983, Methods Enzymol. 100:255–266). Gels were soaked in 10 mM sodium phosphate and capillary blotted onto Hybond-N nylon membrane (Amersham). cDNAs were labelled either using the random primer plus extension reagent labeling system supplied by NEN, and strand specific riboprobes were made using the Stratagene RNA transcription kit. Aqueous hybridizations were done according to the membrane manufacturer's protocol, and blots were washed in 0.1×SSPE, 0.1%×SDS.

6.1.6. Plant Growth Conditions

Progenies of primary transformants previously characterized as expressing GS1 or GS3A at high levels were germinated on Murashige-Skoog (MS) medium containing 100 μg/ml kanamycin. After 14 days kanamycin resistant seedlings were transferred to 4 inch pots filled with white sand, which were covered with Saran Wrap™ for approximately one week to prevent excessive transpiration and enable seedlings to become established. Pots were irrigated periodically with an excess of 1×Hoagland's solution containing 10 mM potassium nitrate as the only nitrogen source. Subsequently between three and seven plants were sacrificed for fresh weight determination each week, continuing for a period of four weeks until shading of neighbors was apparent. Plants were grown under a light-dark cycle of 16–8 h with a temperature cycle of 24–18° C. Daytime light intensity was 1000 lux.

6.2. Results 6.2.1. GS Constructions Introduced Into Transgenic Plants

*Pisum sativum* cDNAs for chloroplastic GS2 (aka GS185 (Tingey et al., 1988, J. Biol. Chem. 263:9651–9657)), cytosolic GS1 (aka GS299 (Tingey et al., 1988, J. Biol. Chem. 263:9651–9657)) and GS3A (aka GS341 (Tingey in et al., 1987, EMBO J. 6:1–9)) were inserted into pTEV binary expression vectors (see FIGS. 3 and 4) for expression behind the CaMV 35S promoter and transferred to transgenic tobacco. For GS2 (construct Z54, FIG. 4) and GS3A (construct Z17, FIG. 4) cDNAs incorporating one or more introns were constructed and expressed behind the CaMV 35S promoter. The purpose of constructing cDNAs incorporating introns was to attempt to enhance expression in transgenic plants, as has been shown for monocots (Sinibaldi and Mettler, 1991, Progress in Nucleic Acid Research and Molecular Biology 42:1991). In addition, unmodified full-length GS cDNAs were also expressed under the 35S-CaMV promoter for GS2 (Z41), G3A (Z9), and GS1 (Z3) (see FIG. 4). For each of the 35S-CaMV-GS constructions detailed in FIG. 4, at least eight primary (T1) transformants were analyzed and representative samples are shown in FIG. 5. For selected primary transformants, four kanamycin-resistant T2 progeny plants were also analyzed (FIG. 6). The analysis of T1 and T2 plants presented below includes Western analysis (FIG. 5 and FIG. 6, panel A); Northern blot analysis (FIG. 6, panel B), GS holoenzyme analysis (FIG. 6, panel C), and GS enzyme activity analysis (FIG. 6, panel C and Tables 1A and 1B) and are representative of all the transgenic lines analyzed.

6.2.2. Analysis of Transgenic Plants Carrying 35S-Chloroplastic GS2 Gene Fusions Transgenic plants containing either of the 35S-GS2 constructs (Z41 or Z54; FIG. 4) were analyzed. Both the 35S-GS2 (Z41) and the modified (intron-containing) 35S-GS2 construct (Z54) gave similar results for both primary T1 transformants and for T2 progeny plants. Western blot analysis of all primary transformants revealed a significant reduction in the abundance of chloroplastic GS2 polypeptide (ctGS) (FIG. 5 lanes 3–6), when compared to wild-type tobacco (FIG.

TABLE 1A

Total GS Activity in Primary Transformants (T1)

| Z41: 35S-GS2 | | Z54:35S-GS2 (modified) | |
|---|---|---|---|
| Z41-6 | 42 | Z54-1 | 13 |
| Z41-7 | 74 | Z54-2 | 11 |
| Z41-8 | 23 | Z54-3 | 49 |
| Z41-12 | 66 | Z54-4 | 22 |
| Z41-14 | 44 | Z54-6 | 39 |
| Z41-15 | nd | Z54-7 | 25 |
| Z41-16 | 65 | Z54-8 | 23 |
| Z41-18 | 29 | Z54-9 | 25 |
| Z41-20 | 35 | Z54-10 | 33 |
| Z41-23 | 76 | | |
| Z41-24 | 32 | | |
| Z41-25 | 67 | | |
| Z41-27 | 29 | | |
| Z41-32 | 22 | | |
| Z41-33 | 85 | | |

| Z17: 35S-GS3 (modified) | | Z3: 35S-GS1 | |
|---|---|---|---|
| Z17-3 | 138 | Z3-1 | nd |
| Z17-6 | 127 | Z3-2 | nd |
| Z17-7 | 119 | | |
| Z17-8 | 36 | | |
| Z17-9 | 45 | | |
| Z17-10 | 52 | | |
| Z17-12 | 28 | | |
| Z17-14 | 145 | | |

Total GS activity was determined for primary transformants and are expressed as percentages compared to SR1 wild-type (=100).
nd - not determined.

TABLE 1B

Total GS Activity in Primary Transformants (T1) and their Progenies (T2)

| | T1 | T2-mean | T2-A | -B | -C | -D |
|---|---|---|---|---|---|---|
| Z41: 35S-GS2 | | | | | | |
| Z41-15 | nd | 27 | 15 | 7 | 75 | 11 |
| Z41-20 | 35 | 50 | 53 | 33 | 31 | 81 |
| Z41-33 | 85 | 35 | 31 | 30 | 32 | 46 |
| Z54: 35S-GS2 (modified) | | | | | | |
| Z54-2 | 11 | 28 | 30 | 19 | 21 | 42 |
| Z54-7 | 25 | 22 | 29 | 21 | 18 | 19 |
| Z54-8 | 23 | 35 | 34 | 39 | 31 | 35 |
| Z17: 35S-GS3A (modified) | | | | | | |
| Z17-6 | 127 | 100 | 112 | 99 | 94 | 96 |
| Z17-7 | 119 | 107 | 104 | 103 | 111 | 108 |
| Z17-9 | 45 | 44 | 126 | 14 | 26 | 11 |
| Z17-10 | 52 | 27 | 33 | 50 | 18 | 5 |
| Z17-12 | 28 | 18 | 21 | 18 | 22 | 10 |

TABLE 1B-continued

Total GS Activity in Primary Transformants
(T1) and their Progenies (T2)

|  | T1 | T2-mean | T2-A | -B | -C | -D |
|---|---|---|---|---|---|---|
| Z3: 35S-GS1 | | | | | | |
| Z3-1 | nd | 123 | 108 | 129 | 113 | 140 |
| Z3-2 | nd | 120 | 114 | 129 | 121 | 116 |

Total GS activity was determined for primary transformants and four T2 progeny plants (labeled A–D). Activity is expressed in percentage of SR1 wild-type (=100).
nd = not determined.

5, lane TL). Since the polyclonal GS2 antibodies have been shown to recognize both pea and tobacco GS2 (Tingey and Coruzzi, 1987, Plant Physiol. 84:366–373; Tingey et al., 1988, J. Biol. Chem. 263:9651–9657) this reduction reflects a down-regulation of both the host tobacco GS2 gene and also of the pea GS2 transgene. No change in the abundance of the cytosolic GS polypeptides (cyGS) was observed in these transformants (FIG. 5, lanes 3–6) compared to control untransformed wild-type tobacco (FIG. 5, lane TL). For Z41, all fourteen independent primary transformants were down-regulated for total GS activity, with a high of 85% wild-type activity to a low of 22% wild-type GS activity (Tables 1A and 1B). For the Z54 constructs, all nine independent primary transformants regenerated were down-regulated to below 50% of wild-type GS activity, with a range of 49% to 11% (Tables 1A and 1B). From these data, it is apparent that the intron containing Z54 constructs were severely co-suppressed. By contrast, the Z41 construct was less efficient at down-regulating endogenous tobacco chloroplastic GS2 and these plants showed a wider range of co-suppression phenotypes (see variation in GS activity amongst Z41 individuals in Tables 1A and 1B). Typically, plants co-suppressed for GS2 (Z54 or Z41) grew more slowly than wild-type and developed intervenial chlorosis (see FIG. 10) due either to the toxicity associated with ammonia accumulation during photorespiration, or glutamine deficiency. These transformants were therefore similar to the previously described GS2 mutants of barley (Wallsgrove et al., 1987, Plant Physiol. 83:155–158). Co-suppressed plants of either Z41 or Z54 type grown in an atmosphere of elevated (1.2%) $CO_2$ (to suppress photorespiration), or supplemented with glutamine, showed less severe symptoms, also supporting the conclusion that these plants were deficient in GS2.

Four kanamycin-resistant T2 progeny plants from primary Z41 and Z54 transformants were also analyzed (FIG. 6). The results obtained from Western analysis and for total GS activity for progenies were similar to those observed for primary transformants (FIG. 6, panel A, and Table 1B). FIG. 6 shows data for one representative T2 progeny member for several Z54 or Z41. primary transformants (FIG. 6, lanes 9–14). Western blot analysis of these plants confirmed the low abundance of the chloroplast GS2 protein (FIG. 6, panel A) and non-denaturing GS activity gel analyses confirmed the reduced abundance of the GS2 holoenzyme (FIG. 6, panel C, lanes 9–14) compared to wild-type tobacco (FIG. 6, panel C, lane TL). Northern analysis showed that transcripts from the GS2 transgene were undetectable (FIG. 6, panel B, lanes 9–14) compared to that present in control pea RNA (FIG. 6, panel B, lane P). These results suggest the specific co-suppression of tobacco chloroplastic GS2 from the insertion of a pea GS2 transgene. In addition, the pea GS2 transgene was also silenced. Levels of cytosolic GS mRNA and protein were unaffected in these GS2 co-suppressed plants.

6.2.3. Analysis of Transgenic Plants Carrying 35-S Cytosolic GS3A Gene Fusions

Transgenic plants containing either type of 35S-GS3A construct (Z17 or Z9; FIG. 4) were analyzed. For Z17 (the intron containing line), of the thirteen independent primary transformants analyzed for GS activity, six showed overexpression of GS activity (119–145%) while seven showed co-suppression (52–28%) compared to untransformed controls (100%) (Tables 1A and 1B). FIGS. 5 and 6 contain data for representative overexpressers and co-suppressed lines of Z17. Transformant Z17-12 is co-suppressed for GS enzyme activity (27% of wild-type) and both chloroplastic GS2 and cytosolic GS proteins are low (FIG. 5, lane 2) compared to wild-type tobacco (FIG. 5, lane TL). By contrast, transformant Z17-6 has elevated levels of total. GS activity (127%) and increased levels of cytosolic GS protein (FIG. 5, lane 1) compared to wild-type tobacco (FIG. 5, lane TL). Analysis of the T2 progeny of other independent transformants revealed additional transformants to be down-regulated for cytosolic GS protein (Z17-9B and Z17-10; FIG. 6, Panel A, lanes 6 and 7), while others had elevated levels of cytosolic GS (Z17-7 and Z17-9A; FIG. 6, Panel A, lanes 4 and 5). The co-suppression phenomenon observed for the Z17 plants (Z17-9B, Z17-10, and Z17-12) is clearly different to that observed for the GS2 transformants (Z54 and Z41) in that both chloroplastic GS2 and cytosolic GS are down-regulated in the GS3A co-suppressed plants (cf. FIG. 6, panel A, lanes 6–8 with lanes 9–14). FIG. 6 shows that co-suppression caused by 35S-GS3A (Z17-9B, Z17-10, Z17-12) is accompanied by reduced GS abundance (from Western and GS activity gel analysis; FIG. 6, panels A and C, lanes 6–8) and virtually undetectable transcription of the GS3A transgene (from Northern analysis; FIG. 6, panel B, lanes 6–8). In transformants overexpressing the GS3A construct (Z17-6, Z17-7, and Z17-9A), the GS3A transcript is very abundant (FIG. 6, panel B, lanes 3–5) and this reflects the greater abundance of cytosolic GS detectable by Western blot analysis (FIG. 6, panel A, lanes 3–5) and GS activity assays (Table 1). Non-denaturing GS activity gel analysis of soluble proteins from these Z17 transformants which overexpress cytosolic GS3A indicates the existence of a novel GS holoenzyme (band A*, FIG. 6, panel C, lanes 3–5) which migrates more slowly than the predominant chloroplast GS2 holoenzyme in wild-type tobacco leaves (band B, FIG. 6, panel C, lane T). It is interesting that individual Z17 transformants carrying the same GS3A transgene construction should give two distinct phenotypes, one of co-suppression (FIG. 6, lanes 6–8) and one of overexpression (FIG. 6, lanes 3–5).

To enlarge the size of the population of transgenic plants analyzed, a second round of transformations was performed and yielded results similar to those described above. Of a total of twenty-three independent primary Z17 transformants analyzed, five were co-suppressed for GS and eight overexpressed GS. In addition, primary transformants were analyzed which contained an unmodified (intron-less) GS3A cDNA (Z9, FIG. 4); of the four Z9 primary transformants analyzed, one was co-suppressed for GS and two overexpressed cytosolic GS. This suggested no qualitative difference between the Z17 (intron containing 35S-GS3A) and Z9 (35S-GS3A cDNA) constructions. Particularly intriguing is the observation that Z17-9A and Z17-9B (FIG. 6, lanes 5 and 6) should have diverse phenotypes as these two T2 plants were derived by self-pollination from a single primary transformant. The Z17-9 primary transformant had been analyzed for total GS activity and found to have reduced activity and therefore to be co-suppressed (see Table 1). Two other T2 progeny plants of Z17-9 were analyzed (Z17-9C and Z17-9D) and these were both found to be co-suppressed giving a ratio of 3:1 in favor of co-suppression in this population.

6.2.4. Analysis of Transgenic Plants Carrying the 35S-Cytosolic GS1 Gene Fusion Transgenic plants containing the 35S-GS1 construct (Z3; see FIG. 4) were also analyzed. Of the eight independent Z3 primary transformants, five gave a clear phenotype of overexpression from Western and Northern blot analysis, and none were co-suppressed. The T2 progeny of two of these Z3 transformants are shown in FIG. 6. Both Z3-1 and Z3-2 show an increased abundance of cytosolic GS protein (FIG. 6, panel A, lanes 1 and 2) and this is reflected by the increased levels of GS mRNA (FIG. 6, panel B, lanes 1 and 2). Non-denaturing activity gel analysis demonstrated a GS holoenzyme (band C) (FIG. 6, panel C, lanes 1 and 2) which migrated faster than the chloroplastic GS2 holoenzyme of tobacco leaves (FIG. 6, panel C, lane T). This faster migrating GS holoenzyme (band C) in the Z3 plants corresponds in size to native pea cytosolic GS.

6.2.5. Analysis of Native and Novel Cytosolic GS Holoenzymes in Transgenic Plants Ectopic expression of cytosolic GS3A (Z17) and GS1 (Z3) gave additional, but different, GS holoenzyme activity bands (e.g., bands A* and C) compared to chloroplast GS2 (band B) seen in wild-type tobacco leaves (FIG. 6, panel C). Electrophoresis of extracts from these transgenic plants was repeated in non-denaturing activity gels including for comparison, lanes of pea root (PR) and tobacco root (TR) protein which are enriched for the cytosolic GS holoenzyme (band C) FIG. 7A, lanes 2 and 4), and extracts derived from purified pea chloroplasts (PC) and tobacco chloroplasts (TC) which are enriched for chloroplastic GS3 holoenzyme (band B) (FIG. 7A, lanes 1 and 3). The additional GS1 holoenzyme activity (band C) seen in extracts of leaves from transgenic tobacco Z3-1 (FIG. 7A, lane 6) co-migrates with the native pea cytosolic GS band (band C, FIG. 7A, lanes 2 and 4). By contrast, the novel GS3A activity (band A*) seen in leaves of the Z17-7 transgenic plants (FIG. 7A, lane 5) co-migrates with neither the cytosolic GS (band C) nor the chloroplastic GS2 band (band B) and is larger in size and more acidic in charge. To determine the subunit composition of the GS activity bands A*, B, and C, these bands were excised from preparative gels, and the extracted proteins were reloaded on a denaturing SDS gel followed by Western blot analysis for GS subunits (FIG. 7B). This analysis revealed that both GS activity band A* and band C are comprised exclusively of cytosolic GS polypeptides (FIG. 7B, lanes 2 and 4). This finding discounted the possibility that the larger GS3A activity band A* was the, result of the assembly of heterologous GS3A cytosolic subunits with endogenous tobacco pre-chloroplastic GS2 subunits. It is possible that GS activity band A* represents the association of transgenic GS3A subunits with a chaperonin-type protein, but attempts to dissociate such a complex with ATP were unsuccessful. Consequently, the nature of the novel GS holoenzyme remains unclear.

6.2.6. Selection of Transformants Ectopically Overexpressing Cytosolic GS1 or GS3A for Growth Analysis Two sets of plants which ectopically overexpress cytosolic GS3A (Z17) or cytosolic GS1 (Z3) were selected for growth analysis. From the first round of transformations (see Experiment A, infra) plants Z3-1 and Z3-2 were selected as GS1 high level expressers (FIG. 6, lanes 1 and 2; FIG. 8, lanes 1 and 2), and plants Z17-6 and Z17-7 were selected as GS3A high level expressers (FIG. 5, lane 1; FIG. 6, lanes 3 and 4; FIG. 8, lanes 3 and 4). Kanamycin resistant T2 progenies of these transformants were selected for growth analysis in experiment A described below. From the second round of transformations, two more independently transformed GS1-overexpressing plants (Z3-3 and Z3-4); (FIG. 8, lanes 5 and 6), and two more independently transformed GS3A-overexpressing plants (Z17-3 and Z17-11): (FIG. 8, lanes 7 and 8) were selected for analysis. The kanamycin-resistant T2 progenies of these plants were analyzed in the second growth experiment (Experiment B, infra).

6.2.7. Design of Plant Growth Experiments

Plant growth analysis was undertaken on the T2, progeny plants analyzed for GS protein and RNA in FIG. 8. Individual T2 plants were grown in white sand and growth was assessed by fresh weight determination of 4–7, plants per time point. Fresh weight measurements were taken only during the vegetative stage of growth when plants were growing rapidly and were exclusively dependent on supplied nitrogen and were not remobilizing large internal sources of nitrogen as might occur during bolting and flowering. Plants were grown under conditions where nitrogen was non-limiting (i.e., regular fertilization with 10 mM nitrate) and which reduced the photosynthetic interference of neighboring plants, and the growth analysis was terminated when such interference became apparent. All plants analyzed were of the same age, and analysis stated at between 0.1 and 0.3 g fresh weight, and continued until the plants were approximately six weeks old when the interference of neighboring plants became apparent at the onset of bolting.

6.2.8. Plant Growth Experiment A

Table 2 shows the results of mean total fresh weight determinations for lines Z3-1 and Z3-2 (overexpressing GS1) and for Z17-6 and Z17-7 (overexpressing GS3A). These results are expressed graphically in FIG. 9, panel A and analyzed statistically in Table 3. All four transgenic lines overexpressing pea cytosolic GS outgrew the control by between 35% and 114%, and this was statistically significant for three lines; Z3-2(P=0.08), Z17-6(P=0.0015) and Z17-7 (P=0.013) (Table 3).

6.2.9. Plant Growth Experiment B

The growth experiment was repeated with different transgenic lines carrying the same GS1 (Z3) and GS3A (Z17) constructions to confirm the results obtained above, including larger plant populations for statistical analysis. Table 2 shows the mean data for four time points for transganic lines Z3-3, Z3-4, Z17-3, and Z17-11, together with two control lines (C1, C2). All lines

TABLE 2

Growth Increase of Transgenic Lines overexpressing Cytosolic GS1 (Z3) or Cytosolic GS3a (Z17)

| Experiment A[1] | C | Z3-1 | Z3-2 | Z17-6 | Z17-7 |
|---|---|---|---|---|---|
| Week 4 | 0.42 | 0.33 | 0.42 | 0.44 | 0.52 |
| Week 5 | 1.40 | 1.88 | 2.36 | 2.73 | 1.91 |
| Week 6 | 4.06 | 5.48 | 8.67 | 8.27 | 6.80 |
| % Increase at week 6 compared to control | 100 | 135 | 214 | 204 | 150 |

| Experiment B[1] | C-1* | C-2* | Z3-3 | Z3-4 | Z17-3 | Z17-11 |
|---|---|---|---|---|---|---|
| Week 3 | 0.12 | 0.07 | 0.32 | 0.24 | 0.32 | 0.20 |
| Week 4 | 0.60 | 0.41 | 1.11 | 0.77 | 1.08 | 1.00 |
| Week 5 | 1.19 | 1.11 | 1.82 | 1.36 | 2.39 | 1.71 |

TABLE 2-continued

Growth Increase of Transgenic Lines
overexpressing Cytosolic GS1 (Z3) or
Cytosolic GS3a (Z17)

| Week 6 | 6.49 | 5.83 | 9.37 | 6.04 | 9.34 | 9.06 |
|---|---|---|---|---|---|---|
| % Increase at week 6 compared to C-1 | 100 | 90 | 144 | 93 | 144 | 140 |

[1]Mean total fresh weight (in grams) of transgenic lines and controls measured over a period of three to four weeks immediately prior to the onset of bolting.
*C-1 is control 1 and C-2 is control 2.

TABLE 3

Growth Increase of Transgenic Lines Over-
expressing Cytosolic GS1 (Z3) or Cytosolic
GS3A (Z17) with Comparison to Controls By
Unpaired T Test

| Experiment A | C | Z3-1 | Z3-2 | Z17-6 | Z17-7 |
|---|---|---|---|---|---|
| week 6 | 4.06 | 5.48 | 8.67 | 8.27 | 6.80 |
| % Increase at week 6 compared to control | 100 | 135 | 214 | 204 | 150 |
| Number of Plants (week 6) | 3 | 6 | 5 | 7 | 6 |
| Standard Error | 0.51 | 0.75 | 1.62 | 0.53 | 0.53 |
| Standard Deviation | 0.88 | 1.85 | 3.62 | 1.41 | 1.28 |
| "T" for unpaired test to control (df) | | 1.23(7) | 2.10(6) | 4.72(8) | 3.29(7) |
| Probability | | 0.26 | 0.08 | 0.0015 | 0.013 |
| Significance | | NS | (*) | ** | * |

| Experiment B | C-1 | C-2 | Z3-3 | Z3-4 | Z17-3 | Z17-11 |
|---|---|---|---|---|---|---|
| week 6 | 6.49 | 5.83 | 9.37 | 6.04 | 9.34 | 9.06 |
| % Increase at week 6 to C-1 | 100 | 90 | 144 | 93 | 144 | 140 |
| Number of Plants (week 6) | 7 | 6 | 7 | 7 | 7 | 7 |
| Standard Error | 0.60 | 1.07 | 0.88 | 0.61 | 1.06 | 0.73 |
| Standard Deviation | 1.58 | 2.61 | 2.33 | 1.61 | 2.81 | 1.94 |
| "T" for unpaired test to C-1 (df) | | | 2.70(12) | 0.53(12) | 2.34(12) | 2.72(12) |
| Probability | | | 0.019 | 0.61 | 0.038 | 0.019 |
| Significance | | | * | NS | * | * |

Mean total fresh weight for transgenic lines (in grams) and controls at week 6. The statistical analysis was done for the final week's measurement only, and in the case of experiment II control-1 (C-1) was selected for the T-test. df—degrees of freedom; The probability of the populations being related was deemed to be highly significant (**) for $P<0.001$, significant (*) for $P<0.05$, and marginally significant ((*)) for $P<0.01$. NS=not significant.
except Z3-4 outgrew controls by between 40 and 44% and the difference in fresh weights at six weeks was statistically significant (Table 3). These results are also shown graphically in FIG. 9, panel B. It is apparent that the second growth experiment corroborated the results of the first, suggesting that ectopic overexpression of wither pea cytosolic GS1 or GS3A enhanced growth rate in tobacco; in all lines tested GS3A overexpression gave an increase in growth rate which was statistically significant increases in growth rate to the transgenic tobacco, compared to non-transformed controls.

6.2.10. Qualitative Effect of GS Overexpression on Plant Growth

FIG. 10 demonstrates a qualitative comparison of the growth phenotype of plants which overexpress GS (Z3-A1 and Z17-B7) to those of control plants and plants co-suppressed for GS (Z54-A2). The results demonstrate that even low level GS overexpression results in readily discernible growth improvements (FIG. 10, compare the growth of Z17-B7 and Z3-A1 with that of control plants). Moreover, these results show that the growth improvements are due to GS overexpression and not to the mere engineering of plants with CaMV-35S GS constructs. For example, Z54-A1, which as been engineered with CaMV 35S-GS2 and was co-suppressed for GS expression, exhibited profoundly poor growth. Furthermore, these results demonstrate that GS activity is a rate limiting step in plant growth as inhibition of this enzyme causes severe phenotypic effects on growth.

6.2.11. Correlation Between GS Activity and Final Fresh Weight and Total Protein Experiments were performed to determine whether changes in GS activity associated with ectopic overexpression or co-suppression of GS genes had an effect on "final" fresh weight at the end of the vegetative growth phase. Growth analysis was performed on T2 generation plants for a line co-suppressed by GS2 (Z54-4), a line overexpressing GS1 (Z3-1), a line overexpressing GS3A (Z17-7), and an untransformed tobacco control (SR1). Plants were grown in sand and irrigated periodically with Hoagland's solution containing 10 mM $KNO_3$. At designated time-points, eight individual T2 plants from each line were weighed and leaf GS activity was determined for each individual. Analysis of this, data reveals a linear relationship between "final" fresh weight and GS specific activity for all individuals assayed at both 32 days and 43 days (FIG. 11A). For example, Z54-4 plants which are co-suppressed for GS activity (27% of wild-type GS activity) weigh one-half as much as controls, while plants which overexpress GS3A (136% GS activity) or GS1 (284% GS activity) out-weigh controls by 1.5-times and 2-times, respectively. For these same individual T2 plants, a linear relationship also exists between total leaf protein ($\mu$g protein/gm fresh weight) and leaf GS activity. Plants expressing the highest levels of GS activity (284%) had 1.5-fold higher levels of soluble protein/gram fresh weight compared to controls (FIG. 11B). An unpaired T-test analysis of this data revealed that the GS overexpressing lines (Z3-1,Z17-7) had significantly greater GS activity, fresh weight, and leaf soluble protein with a p value of <0.0001, with the exception of fresh weight for Z17-7 whose p value was 0.0007. Similarly the line co-suppressed by GS2 (Z54-4) had significantly less GS activity, fresh weight, and leaf soluble protein than control SR1 with a p value of <0.0001. The GS activity profiles of the GS overexpressing T2 lines used in the growth study (Z3,Z17) parallel the parental T0 lines and the T1 progeny, except that the GS activities were consistently higher in the T2 generation. This is most likely due to the fact that some or all of the transgenes became homozygous in the T2 generation, as there was no observed segregation of the Kan[R] phenotype associated with the GS transgene. At the end of the growth experiment, the transgenic lines overexpressing GS were visibly greener and dramatically larger than controls.

6.3. Discussion

As genetic engineering begins to assume significance in crop plant improvement it is becoming increasingly important to understand the parameters critical in the overexpression of selected genes. It is apparent that the overexpression of genes for which there are host plant homologs may be more complex than the overexpression of genes for which there are no homologs, such as viral coat protein and BT toxin genes (Powell-Abel et al., 1986, Science 232:738–743; Vaeck et al., 1987, Nature 328:33–37). This is due to the phenomenon of co-suppression in which the transgenic plant can detect and silence a transgene to which there is a host homolog, perhaps by feedback inhibition or some other mechanism (van der Krol et al., 1990, Plant Cell 2:291–299; Napoli et al., 1990, Plant Cell 2:279–289). Presented here is an effort to ectopically overexpress three different pea GS genes for chloroplast or cytosolic GS behind the sane constitutive promoter (35S-CaMV) in transgenic tobacco. The effort resulted in overexpression and/or co-suppression that is different for each GS gene. Furthermore, for the two genes for cytosolic GS which were successfully overexpressed (GS1 and GS3A), the overexpression resulted not only in over production of GS RNA, protein and enzyme, but also in a phenotype of improved nitrogen use efficiency.

Overexpression of the pea gene for cytosolic GS1 in tobacco gives a clear phenotype of increased GS activity, increased cytosolic GS protein, and high levels of transgene mRNA. Furthermore, the GS1 protein assembles into a GS holoenzyme similar in size and charge to native pea cytosolic GS. In transgenic plants overexpressing cytosolic GS3A, the situation is somewhat different. High levels of GS3A transgene mRNA give rise to increased levels of cytosolic GS which are visible on Western blots. However, the overexpression of GS3A causes the appearance of a novel GS holoenzyme which is larger than the native chloroplastic or cytosolic GS holoenzymes of either pea or tobacco. In these transgenic plants, the cytosolic GS gene was being expressed in a cell type where it is not normally found (e.g., mesophyll cells), and it was possible that the larger GS holoenzyme in the GS3A transgenic leaves was due to the co-assembly of cytosolic CS subunits with native pre-chloroplast GS2. However, this novel GS3A holoenzyme was shown to be composed exclusively of cytosolic GS subunits and was therefore not due to the co-assembly of transgenic GS3A subunits with endogenous tobacco pre-chloroplastic GS2. Two other possibilities exist. The larger GS3A holoenzyme may be the result of transgenic GS3A subunits assembling into a configuration other than their usual octameric structure. Alternatively, the novel GS3A holoenzyme may result from the failure of the overexpressed cytosolic subunits to be released from an assembling chaperonin. Indeed, the close association of GS with groEL-like proteins has previously been observed in pea (Tsuprun et al., 1992, Biochim. Biophys. Acta 1099:67–73). However, our attempts to dissociate the novel GS3A activity band from a potential chaperonin using ATP were unsuccessful. Although the novel GS3A holoenzyme must clearly possess GS activity (from its detection in GS activity gel analysis) it is interesting to speculate whether or not this novel GS isozyme possesses a similar activity to the native cytosolic GS or chloroplastic GS2 holoenzymes on an equimolar basis. If this is the case, it might be predicted that plants overexpressing 35S-GS3A, and therefore possessing the novel GS holoenzyme, may have elevated total GS activities. In fact this was not the case; the mean total GS activity (compared to wild-type) of four Z17-6 T2 progeny plants (expressing GS3A) was found to be 100%, and that of four Z17-7 progeny plants was 107% compared to wild-type. By contrast, GS activity values obtained for T2 progenies of Z3-1 and Z3-2 (overexpressing a GS1 native holoenzyme) were 123% and 120% respectively, compared to wild-type. This suggests that the assembly in the GS1 subunits in the Z3 overexpressing transformants into a GS holoenzyme of native size was advantageous to total GS activity.

Here, nitrogen use efficiency was assessed during the vegetative growth stage of transgenic tobacco which successfully overexpressed wither cytosolic GS1 or cytosolic GS3A. During vegetative growth there is rapid leaf development characterized by rapid nutrient uptake and the maximization of photosynthetic capacity. Nitrogen is the most frequently limiting micronutrient, and the physiology of its uptake and use within the plant differs between the vegetative and generative stages. firstly there is nitrogen incorporation from the soil, its incorporation into expanding tissues, and the limitation of losses through photorespiration and subsequently, with the onset of bolting, there is the mobilization of nitrogen reserves for conversion to seed yield during the generativestage of growth. It is likely that the parameters of nitrogen use efficiency are less complex during the vegetative growth stage of development, and our transgenic plant growth analysis has focused on this stage of growth.

The present findings indicate that ectopically expressed pea cytosolic glutamine synthetase in tobacco provides a considerable advantage in the vegetative growth stage of transgenic tobacco. Plants which overexpress either cytosolic GS1 or GS3A ectopically (i.e., in all cell types) yield a higher total fresh weight that controls. It was particularly striking that all GS3A expressing lines (Z17) had higher total fresh weights than controls at six weeks and these were always statistically significant. In each case there was a less than a 5% chance that the difference between control and transgenic lines was due to sample variance. For the GS1 expressing lines analyzed (Z3), three out of four outgrew controls and for two of these the difference was statistically significant at the 10% level. This increased use efficiency of nitrogen may enable crops to be similarly engineered to allow better growth on normal amounts of nitrogen or cultivation with lower fertilizer input, or alternatively on soils of poorer quality and would therefore have significant economic impact in both developed and developing agricultural systems.

Although GS-overexpression has previously been attempted in transgenic tobacco (Eckes et al., 1989, Mol. Gen. Genet. 217:263–268; Hemon et al., 1990, Plant Mol. Biol. 15:895–904; Hirel et al., 1992, Plant Mol. Biol. 20:207–218; Temple et al., 1993, Mol. Gen. Genet. 236:315–325), this is the first report in which overexpression of GS is correlated with a significant increase in GS activity and an improvement in plant growth and nutritional characteristics. Temple et al. reported increases in GS mRNA and protein, but no corresponding increase in GS activity in the transgenic plants (Temple et al., ibid). Hemon et al. reported increased levels of GS mRNA in transgenic plants engineered with GS expression constructs, but found no corresponding increase in GS protein or enzyme activity (Hemon et al., ibid). In two other reports, overexpression of GS genes in transgenic plants did result in increased levels of GS enzyme, but the studies reported no phenotypic effects of GS overproduction (Eckes et al., ibid; Hirel et al., ibid). There is one report of overexpression of an alfalfa GS gene improving plant growth rate by about 20% (Eckes et al., 1988, Australia Patent Application No. AU-A-17321/88).

However, this reported improvement appears to be limited to growth under low-nitrogen conditions only. Identically engineered plants were reported to show no phenotypic changes, as compared to control plants, in a subsequent analysis carried out on a nitrogen non-limiting medium (Eckes et al., 1989, Mol. Gen. Genet. 217:263–268). In addition, there is no report that the faster rate of growth results in difference in final fresh weight between the engineered and control plants. In contrast to these earlier studies, the instant invention demonstrate unequivovally that, regardless of the nitrogen conditions, GS overexpression can improve growth, yield, and/or nutritional characterisitics of plants.

The agricultural utility of the instant invention is directly relevant to crop species in which the vegetative organs are harvested, and these include all forage crops, potato, sugar beet, and sugar cane as well as tobacco. Within a week of the final fresh weight recordings presented here, plants started to undergo internode extension, and the standard deviation of subsequent fresh weight measurements for each population increased as a result of the differing physiological stage of plants. Whether the increased vegetative growth rate would also lead to a significant seed yield advantage is an important question which remains to be answered. The physiological parameters relevant to seed yield and seed nitrogen content include not only the efficiency of nitrogen uptake, but also the remobilization of reserves at the onset of bolting, and the consequences of field population density. Such studies would be better undertaken in a transgenic species which has been selected for seed yield and for which there is some understanding of yield physiology.

The finding that co-suppression of endogenous tobacco GS by genes encoding chloroplastic GS2 and cytosolic GS3A of pea, but not by cytosolic GS1 is also intriguing. This is especially so as pea GS2 suppresses only the tobacco chloroplastic GS2 form while GS3A suppresses both tobacco chloroplastic GS2 and cytosolic GS. Previously, Petunia chalcone synthase and dihydroflavanol-4-reductase have been shown to co-suppress both endogenous and transgenes in transgenic Petunia (van der Krol et al., 1990, Plant Cell 2:291–299; Napoli et al., 1990, Plant Cell 2:279–209). More recently it has been reported that either the 5' or the 3' end of the chalcone synthase gene was sufficient to cause co-suppression, but that a promoter-less gene was not (Jorgensen, 1992, Agbiotech News and Information September:1992), suggesting the necessity of transcriptional initiation. Transient ectopic sequence pairing has been invoked as a possible mechanism for gene silencing and this may depend on the unwinding of DNA presumably associated with the initiation of transcription (Jorgensen, 1990, Trends in Biotechnology 8:340–344; Jorgensen, 1991, Trends in Biotechnology 9:255–267; Jorgensen, 1992, Agbiotech News and Information September:1992). From the present findings on pea GS gene expression it appears that the co-suppression phenomenon does not depend on perfect sequence homology at the nucleotide level.

Increasing nitrogen use by modifying the expression of nitrogen assimilatory enzymes may also be a feasible approach to enhancing yields in transgenic crop plants such as corn. The efficiency of nitrogen use in crops is measured as enhanced yields and is therefore an agricultural measure. This kind of adaptation or specialization would be of no real advantage to wild type plants which depend for their survival on a diversity of responses to environmental conditions and not on higher yields (Sechley et al., 1992, Int. Rev. Cyt. 134:85–163). Therefore, increases in crop yield may be more easily realized through genetic engineering methods such as those described herein, rather than by conventional breeding methods.

7.0. EXAMPLE

Ectopic Overexpression of Asparagine Syntretase in Plants Causes an Increase in Plant Growth Phenotype The following study concerns the manipulation of AS gene expression in plants with the aim of increasing asparagine production and testing the effects on plant growth. There are several features of asparagine which make it preferable to glutamine as a nitrogen transport/storage compound and hence the increased assimilation of nitrogen into asparagine may be valuable in vivo. Asparagine is a long-distance nitrogen transport compound with a higher N:C ratio than glutamine. It is therefore a more economical compound for nitrogen transport. In addition, asparagine is more stable than glutamine and can accumulate to high levels in vacuoles (Sieciechowicz et al., 1988, Phytochemistry 27:663–671; Lea and Fowden, 1975, Proc. R. Soc. Lond. 192:13–26). In developing pea leaves, asparagine is actively metabolized, but in mature leaves that no longer need nitrogen for growth, asparagine is not readily metabolized and is re-exported (in the phloem) from the leaf to regions of active growth such as developing leaves and seeds (Sieciechowicz et al., 1988, Phytochemistry 27:663–671; Ta et al., 1984, Plant Physiol 35 74:822–826). AS is normally only expressed in the dark (Tsai and Coruzzi, 1990, EMBO J. 9:323–332) therefore 35-AS1 is expressed constitutively and not only ectopically expressed in regard to cell type, but also in regard to temporal expression. Thus, the studies presented here examined whether the ectopic overexpression of AS in all cell-types in a light-independent fashion would increase asparagine production. Also tested here was whether the increased asparagine production provides an advantage in the nitrogen use efficiency and growth phenotype of transgenic plants.

In addition to overexpression wild-type AS, the present study also examined the ectopic overexpression of a modified form of the AS enzyme (gln$\Delta$AS1) which was missing the glutamine-binding domain. A question addressed by this study was whether ectopic overexpression of a gln$\Delta$AS1 form of the enzyme might produce a novel plant AS enzyme with enhanced ammonia-dependent AS activity or whether such a mutation may have a dominant-negative effect (Herskowitz, 1987, Nature 329:219–222) due to co-assembly with endogenous wild-type AS subunits to form a heterodimer (Rognes, 1975, Phytochemistry 14:1975–1982; Hongo and Sato, 1983, Biochim et Biophys Acta 742:484–489). The analysis of the transgenic plants which ectopically express pea AS, demonstrated an increased accumulation of asparagine and an improved growth phenotype (in the case of 35S-AS1), and an increased accumulation of asparagine but accompanied by a detrimental effect on growth phenotype (in the case of 35S-gln$\Delta$AS1). These results indicate that it is possible to manipulate nitrogen metabolism and growth phenotype by ectopic overexpression of AS genes. Because nitrogen is often the rate-limiting element in plant growth and typically applied to crops several times during the growing season, designing molecular technologies which improve nitrogen use efficiency in crop plants is of considerable interest to agriculture.

7.1. Materials and Methods
7.1.1.. AS Gene Constructs

The AS1 cDNA previously cloned from pea (Tsai and Coruzzi, 1990, EMBO J 9:323–332) was transferred from pTZ18U to the EcoRI site of pBluescript KS- (Stratagene).

A glnΔAS1 deletion mutant was constructed using "inside-outside" PCR (Innis et al., 1990, PCR Protocols: A guide to Methods and Applications. New York, Academic Press pp.1–461). Coding sequence corresponding to amino acids 2–4 (CGI) was deleted from the amino terminus of the AS1 cDNA, leaving the initiating methionine and the untranslated leader intact. This deletion corresponded to the presumed glutamine-binding domain of the AS enzyme comprising amino acids MCGI which have been defined for animal AS (Pfeiffer et al., 1986, J. Biol. Chem. 261:1914–1919; Pfeiffer et al., 1987, J. Biol. Chem. 252:11565–11570). cDNAs corresponding to wild-type As1 and glnΔAS1 were then transferred from pBluescript to the binary expression vector pTEV5. This vector contains the CaMV 35S promoter (from −941 to +26), a multiple cloning site, and the nopaline synthase terminator. FIG. 12 shows details of the binary vector constructions containing the AS1 cDNAs pZ127 (NRRL Accession No. B-21335) and glnΔAS1 cDNA pZ167 (NRRL Accession No. B-21336), which were transformed into tobacco.

7.1.2. Plant Transformations

Binary vector constructions were transferred into the disarmed Agrobacterium strain LBA4404 and subsequently into *Nicotiana tabacum* SR1 using standard procedures described elsewhere (Bevan, 1984, Nucleic Acids Res. 12:8711–8721; Horsch et al., 1985, Science 227:1229–1231).

7.1.3. RNA Analysis of Transformants

RNA was isolated using "RNA matrix" from Bio101 and total RNA was electrophoresed as previously described (Thomas, 1983, Methods Enzymol. 100:255–266). Gels were capillary blotted onto Hybond-N nylon membrane (Amersham). cDNAs were labeled using the random primer plus extension reagent labeling system supplied by NEN. Hybridizations were done in aqueous solution and blots were washed in 0.1×SSPE, 0.1% SDS. Northern blots were robed with the pea AS1 cDNA, pAS1 (Tsai and Coruzzi, 1990, EMBO J 9:323–332).

7.1.4. Extraction of Free Amino Acids

Tobacco leaf tissue samples were frozen in liquid nitrogen and extracted in 10 mls of extraction media consisting of methanol:chloroform:water (12:5:3, v/v/v). The homogenate was centrifuged at 12,000 ×G for 15 minutes. The pellet was extracted again and the supernatants were combined. Addition of 2.5 ml chloroform and 3.8 ml of distilled water to the supernatant induced separation. The methanol:water phase was collected and dried under vacuum and redissolved in 1 ml of distilled water. The solution was filtered by passing it through a 0.45 μm nylon filter microcentrifuge tube filter system centrifuged at 12,000 g for 2 min.

7.1.5. HPLC Determination of Amino Acid Pools

The amino acids were determined as o-phthaldialdehyde (OPA) derivatives on a Microsorb Type O AA Analysis column (Rainin) using a DuPont HPLC instrument. Sample (100 μL) was derivatized with 100 μl of OPA working reagent. After 2 min of derivatization, 50 μL of the derivatized sample was injected. This gradient was produced using two eluents: A. 95% 0.1 M sodium acetate (pH 7.2) with 4.5% methanol and 0.5% tetrahydrofluoran; B. 100% methanol. Eluents were filtered and degassed with He before use. Detection of OPA derivatized amino acids was accomplished with a UV spectrophotometer at 340 nm. Each determination was done twice and the values represent the average.

7.1.6. Plant Growth Conditions

Progenies of primary transformants characterized as expressing high levels of either as AS1 mRNA or the mutated glnΔAS1 mRNA were germinated on MS-medium containing 100 μg/ml kanamycin. After 14 days, kanamycin resistant seedlings were transferred to 4 inch pots filled with white sand, which were covered with saran wrap for approximately one week to prevent excessive transpiration and enable seedlings to become established. Pots were irrigated periodically with 1×Hoagland's solution containing 10 mM potassium nitrate as the only nitrogen source. Subsequently, between three and seven plants were sacrificed for fresh weight determination each week, continuing for a period of four weeks until shading of neighbors was apparent. Plants were grown under a light-dark cycle of 16–8 h with a temperature cycle of 24–18° C. Daytime light intensity was 1000 lux.

7.2. Results

7.2.1. Construction of Transgenic Plants Expression Pea AS1 and GLNΔAS1

The pea AS1 cDNA (Tsai and Coruzzi, 1990, EMBO J 9:323–332) expressed from the 35S-CaMV promoter was transferred into transgenic tobacco (See FIG. 12 and Section 7.1 Material and Methods) and five independent primary transformants (Z127; 1–5) were shown to express high levels of the AS1 mRNA (see below). Three independent transgenic lines (Z167;1–3) which contained the AS1 cDNA with a deletion in the glutamine binding domain (glnΔAS1) were also shown to contain high levels of transgene RNA (see infra).

7.2.2. Northern Analysis of Transformants Expression AS1 and GLNΔAS1

Northern blot analysis of RNA extracted from transgenic plants were undertaken to identify plants in which the 35S-AS1 transgene was expressed at high levels (FIG. 13). As a positive control, RNA for AS was detected in leaves of pea plants grown in the dark (FIG. 13, lane PL). By contrast, no AS mRNA was detected in leaves of light-grown wild-type tobacco (FIG. 13, TL). Previous studies have shown that tobacco AS mRNA is expressed exclusively in tissues of plants grown the dark (Tsai and Coruzzi, 1991, Mol Cell Biol 11:4966–4972). The transformants which overexpress AS1 (Z127-1, -3, -4, and -5) all contained high levels of AS1 mRNA, even though these plants were grown in the light (FIG. 13). Thus, the 35S CaMV promoter produces constitutive expression of pea AS1, whereas the endogenous AS mRNA is not expressed in tobacco leaves in the light. The glnΔAS1 transformants also showed constitutive high level expression of mRNA (Z167-2, -3, and -4), compared to tobacco controls (FIG. 13). Because the AS enzyme is notoriously unstable, the AS enzyme has never been purified to homogeneity and antibodies for plant AS were not available for AS protein analysis. In addition, in vitro assay detected no AS activity due to enzyme instability.

.7.2.3. Amino Acid Analysis of Transgenic Lines Expressing AS1 and GLNΔAS1

Based on the Northern results, two independent transgenic lines which showed high levels of AS1 mRNA (Z127-1 and Z127-4) were selected for further analysis. Similarly, lines Z167-2 and Z167-4 were selected as high-expressing representatives of the glnΔAs1 construction. The T2 progenies of these plants were subjected to amino acid and growth analysis described below.

7.2.4. AS1-Overexpressing Lines

Both Z127 lines selected (Z127-1 and Z127-4) showed increased levels of asparagine (10- to 100-fold higher than wild-type controls) (Table 4). The variation apparent among the individual T2 plants most likely reflects the homozygosity or heterozygosity of individuals, and the approximate 2:1 ratio of intermediate:high asparagine levels would substantiate this assertion. In all cases, however, a considerable increase in asparagine is seen extending up to nearly 100-times the control concentration. Interestingly, there is a corresponding reduction in glutamine concentrations in these plants (although the Z127-4 data is skewed by a single high value) and this reflects the use of glutamine as a substrate in the AS reaction; equally predictable is the reduction in concentration of the other substrate aspartate. Somewhat unexpected, however, is the reduced concentration of glutamate in the Z127 lines. From biochemical predictions and from the data collected for the other three amino acids involved in the AS reaction, an increase in glutamate would have been predicted. The apparent reduction in glutamate may be the result of its high turnover rate due to its use as a substrate in several related processes such as transamination.

7.2.5. GLNΔAS1-Overexpressing Lines

In the two lines selected which overexpress glnΔAS1, the question assessed was whether the deletion of the glutamine-binding domain of AS would have a dominant-negative effect on asparagine biosynthesis. The data collected for these lines (Z167-2 and Z167-4) is somewhat difficult to interpret due to the variation of data values (Table 4). However, in almost every case there is a substantial increase in asparagine concentration, ranging from 3- to 19-fold compared to wild-type non-transgenic tobacco. These results suggest that the transgenic lines have the ability to accumulate asparagine with little effect on aspartate, glutamate or glutamine pools. One possibility is that the glnΔAS1 enzyme is able to synthesize asparagine directly from ammonia and aspartate.

7.2.6. Plant Growth Experiment on Transformants Expressing AS1 and GLNΔAS1

Growth analysis was undertaken using individual transgenic T2 plants grown in white sand. These studies were aimed at assessing growth rate under conditions which minimized interference from neighboring plants. For this reason, fresh weight measurements were taken only during the vegetative stage of growth (up to six weeks post germination). During this period, plants undergo rapid growth and are exclusively dependent on supplied nitrogen and do not remobilize internal nitrogen sources as might occur during bolting and flowering. Plants were grown under conditions where nitrogen was non-limiting (i.e., regular fertilization with 10 mM nitrate) and which reduced the photosynthetic interference of neighboring plants. The growth analysis was terminated when such interference became apparent. All plants analyzed were of the same age at each time point, and analysis started at between 0.1 and 0.3 g fresh weight/plant, and continued until the plants were approximately six weeks old when the interference of neighboring plants became apparent and bolting was imminent.

TABLE 4

Amino Acid Analysis in Transgenic Lines Overexpressing AS1 or glnΔAS1

| PLANT ID | ASN | GLU | GLN | ASP |
|---|---|---|---|---|
| CONTROL | | | | |
| C | 34 | 1399 | 309 | 1935 |
| C | 38 | 1425 | 405 | 1861 |
| C | 36 | 965 | 425 | 2015 |
| C | 47 | 1526 | 275 | 1720 |
| mean | 39 | 1335 | 353 | 1883 |

TABLE 4-continued

Amino Acid Analysis in Transgenic Lines Overexpressing AS1 or glnΔAS1

| PLANT ID | ASN | GLU | GLN | ASP |
|---|---|---|---|---|
| AS1 wild-type | | | | |
| Z127-1-A | 553 | 228 | 14 | 182 |
| Z127-1-B | 3399 | 808 | 60 | 922 |
| Z127-1-C | 213 | 525 | 81 | 240 |
| Z127-1-D | 487 | 537 | 17 | 264 |
| Z127-1-E | 3159 | 983 | 43 | 796 |
| mean | 1562 | 616 | 43 | 481 |
| Z127-4-A | 1105 | 838 | 132 | 451 |
| Z127-4-B | 902 | 2947 | 389 | 1092 |
| Z127-4-C | 373 | 1606 | 17 | 678 |
| Z127-4-D | 4109 | 691 | 923 | 1664 |
| mean | 1622 | 1520 | 365 | 971 |
| glnΔAS1 | | | | |
| Z167-2-A | 684 | 838 | 352 | 761 |
| Z167-2-B | 1341 | 2947 | 944 | 3119 |
| Z167-2-C | 173 | 1606 | 1224 | 1946 |
| mean | 733 | 1797 | 840 | 1942 |
| Z167-4-A | 47 | 691 | 75 | 948 |
| Z167-4-B | 109 | 864 | 346 | 1491 |
| Z167-4-C | 137 | 1313 | 714 | 1705 |
| Z167-4-D | 165 | 1534 | 838 | 2069 |
| mean | 114 | 1100 | 493 | 1553 |

Amino acid concentrations are in nmol/gram fresh weight

TABLE 5

Growth Increase of Transgenic Lines Overexpressing AS1 or glnΔAS1

| | C-1 | C-2 | Z127-1 | Z127-4 | Z167-2 | Z167-4 |
|---|---|---|---|---|---|---|
| 3 | 0.12 | 0.07 | 0.28 | 0.12 | 0.11 | 0.19 |
| 4 | 0.60 | 0.41 | 1.30 | 0.51 | 0.31 | 0.57 |
| 5 | 1.19 | 1.11 | 1.87 | 1.72 | 0.71 | 0.99 |
| 6 | 6.49 | 5.83 | 8.63 | 7.16 | 3.83 | 6.13 |
| % increase at week 6 compared to C-1 | 100 | 90 | 133 | 110 | 59 | 94 |

Total fresh weight means (in grams) of transgenic lines and controls measured over a period of three to four weeks immediately prior to the onset of bolting.

Tables 5 and 6 show the results of mean total 25 fresh weight determinations for lines Z127-1 and Z127-4 (overexpressing wild-type AS1) and Z167-2 and Z167-4 (overexpressing glnΔAS1), and these results are expressed graphically in FIG. 13. Transgenic lines overexpressing wild-type AS grew 133% and 110% compared to control (100%) (Table 5), although in neither case was this statistically significant when analyzed by unpaired T-test (Table 6). Transgenic lines overexpressing the glnΔAS1 construction (Z167) did not perform comparably. The Z167-4 plants which survived until the sixth week were indistinguishable in growth from controls, and the Z167-2 plants which survived, were such smaller than controls (P-0.041; significant at the 5% level) (Tables 5 and 6, and see also FIG. 14). Comparing the three different lines in the experiment, it was of interest that a greater proportion of kanamycin resistant Z167 plants died. Typically the Z167 plants were slow to germinate and looked unhealthy when grown in pots. This was clearly reflected in the fresh weight data collected for Z167-2, although less apparent for the Z167-4 data, suggesting that the glnΔAS1 gene product did indeed have a dominant-negative effect on plant growth.

TABLE 6

Growth Increase of Transgenic Lines Overexpressing AS1 or glnΔAS1 with Comparison to Controls By Unpaired T Test

|  | C-1 | C-2 | Z127-1 | Z127-4 | Z167-2 | Z167-4 |
|---|---|---|---|---|---|---|
| Week 6 | 6.49 | 5.83 | 8.63 | 7.16 | 3.83 | 6.13 |
| % Increase at week 6 compared to control 1 | 100 | 90 | 133 | 110 | 59 | 94 |
| Number of Plants (week 6) | 7 | 6 | 7 | 7 | 3 | 5 |
| Standard Error | 0.60 | 1.07 | 1.15 | 0.88 | 0.92 | 0.85 |
| Standard Deviation | 1.58 | 2.61 | 3.05 | 2.34 | 1.60 | 1.89 |
| "T" for unpaired test to control-1 (df) |  |  | 1.65 (12) | 0.63 (12) | 2.43 (8) | 0.35 (10) |
| Probability |  |  | 0.125 | 0.54 | 0.041 | 0.731 |
| Significance |  |  | NS | NS | * | NS |

Total fresh weight means for transgenic lines (in grams) and controls at week 6. The statistical analysis was done for the final week's measurement only and control-1 was selected for the T-test df - degrees of freedom; The probability of the populations being related was deemed to be significant (*) for $P < 0.05$; NS - not significant

7.3. Discussion

Reported here are studies in which AS is ectopically overexpressed in transgenic plants to test the effects of this manipulation on primary nitrogen assimilation and on plant growth. In particular, the cell-specific expression pattern of AS were altered and the regulation of AS with regard to light was also modified. In wild-type plants, AS is normally only expressed in the phloem (Tsai, 1991, Molecular Biology Studies of the Light-Repressed and Organ-Specific Expression of Plant Asparagine Synthetase Genes. Ph.D. Thesis, The Rockefeller University, New York, N.Y.), and its expression is dramatically repressed by light in both photosynthetic and non-photosynthetic tissues (Tsai and Coruzzi, 1990, EMBO J 9:323–332; Tsai and Coruzzi, 1991, Mol Cell Biol 11:4966–4972). Here, the wild-type AS1 of pea and a mutated form of AS1 (glnΔAS1) were expressed under the control of a constitutive promoter (35S-CaMV) in transgenic tobacco so that AS1 is expressed in all cell types, in a light-independent fashion. The physiological significance of constitutively expressing AS1 in cells where it is not normally expressed may have considerable impact on plant nitrogen metabolism. For example, asparagine is involved in photorespiratory nitrogen recycling (Givan et al., 1988, TIBS 13:433–437; Ta et al., 1984, Plant Physiol 74:822–826), thus the ectopic expression of AS in photosynthetic cells may have dramatic impact on photorespiration. Furthermore, the expression of an ammonia dependent AS enzyme in this context may aid in the reassimilation of photorespiratory ammonia.

Four independent transgenic tobacco lines expressing 35S-AS1 have been shown to express a wild-type pea AS1 transgene constitutively. Two lines were analyzed further (Z127-1 and Z127-4) and it was shown that the expressed AS1 gene was functional since free asparagine accumulated to high levels in transgenic leaf tissue; typically transgenic lines Z127-1 and Z127-4 accumulated between 10- and 100-fold more asparagine than control untransformed tobacco lines. These increased asparagine levels were predictably accompanied by a reduction in the AS substrates, glutamine and aspartate. However, it may still be possible to channel more inorganic nitrogen into the nitrogen transport compound asparagine by providing higher endogenous levels of glutamine, a substrate for AS.

The plant growth experiment on the Z127 transgenic plants was aimed at determining whether the accumulation of asparagine in the AS1 overexpressing plant might have a positive effect on growth during the vegetative stage of plant development. The rapid leaf development which occurs during vegetative growth imposes a strong demand for nutrient availability and nitrogen is typically the most critical nutrient at this time due to the synthesis of new proteins in expanding and enlarging tissues. Nitrogen assimilated and accumulated at this time is subsequently recycled in the plant and deposited in seed reserves; as well as being a major long-distance transport amino acid, asparagine also plays an important role in the formation of seed reserves (Dilworth and Dure, 1978, Plant Physiol 61:698–702; Sieciechowicz et al., 1988, Phytochemistry 27:663–671). The two Z127 lines were found to outgrow untransformed controls over a six week period up to the end of vegetative growth and conferred a 10% and a 33% growth advantage. However, these figures were not statistically significant when a T-test is performed. Thus, although the plants make 10- to 100- fold higher levels of asparagine it is possible that glutamine levels are limiting relative to increases in growth. Also presented here is the finding that overexpressing GS in transgenic tobacco can confer a greater growth advantage which is statistically significant (supra). As glutamine is a substrate for asparagine biosynthesis both are pivotal amino acids in the primary assimilation of inorganic nitrogen. It can therefore be anticipated that creating transgenic lines which express both GS and AS at high levels (by crossing AS and GS overexpressers) may have even more advantageous growth traits than either parent. In particular, the approaches disclosed here have the advantage that assimilation in transgenic lines will not be restricted to a few cell types, enabling available nitrogen in all plant cells to be utilized. The ectopic overexpression of both GS and AS in a single plant may have the advantage of avoiding glutamine accumulation; since glutamine is an active metabolite in the presence of high concentrations of glutamine may upset cell metabolism. By contrast, asparagine is a relatively inert compound able to store nitrogen economically. In addition, asparagine is formed in a reaction which liberates a molecule of glutamate then available to accept a further unit of ammonia (Lea and Fowden, 1975, Proc. R. Soc. Lond. 192;13–26).

In addition to the ectopic overexpression of wild-type AS, the plant glutamine-dependent AS was modified in an attempt to enhance its ammonia-dependent activity. In particular, it has been shown in animals that antibodies to the glutamine-binding domain of AS inhibit glutamine-dependent AS activity present on the same AS polypeptide, yet enhance the ammonia-dependent activity (Pfeiffer et al., 1986, J. Biol. Chem. 261:1914–1919; Pfeiffer et al., 1987, J. Biol. Chem. 252:11565–11570). By analogy, a site-specific mutant was created in a pea AS1cDNA (Tsai and Coruzzi, 1990, EMBO J 9:323–332) which mutation specifically deleted the three amino acids required for glutamine binding (glnΔAS1). By introducing this glnΔAS1 into transgenic plants, it might be possible to enhance the ammonia-dependent AS activity and/or inhibit the endogenous glutamine-dependent AS activity through subunit poisoning and the formation of heterodimers of wild-type and mutant subunits. Two independent transgenic lines, Z167-2 and Z167-4, which overexpress the gln6AS1 transgene were found to be capable of accumulating asparagine levels approximately 3- to 19-times greater than untransformed tobacco controls. The activity of the glnΔAS1 gene in assimilating asparagine is suggestive of the modified enzyme having the capability of utilizing a nitrogen substrate other than glutamine (e.g.,.ammonia). By analogy to the known ammonia-dependent AS activities of the *E. coli* AsnA gene and mammalian AS, the high levels of asparagine in the transgenic plants which express the mutated plant glnΔAS1 enzyme suggest that the glnΔAS1 enzyme can assimilate ammonia directly into asparagine and therefore bypass GS in primary nitrogen assimilation. If this suggestion is correct, it is also apparent that the glnΔAS1 gene is not as efficient in synthesizing asparagine as the overexpressed wild-type AS1, based on the relative levels of asparagine in these transgenic plants (Z167 vs. Z127).

Transgenic lines expressing glnΔAS1 (Z167-2 and Z167-4) did not outgrow untransformed controls; indeed they typically grew more poorly than untransformed plants as evidenced by the performance of Z167-2 and the higher proportion of Z167 plants to die before the end of the experiment. It is curious that these plants should accumulate 3- to 19-fold higher levels of asparagine in their leaves, yet grow more poorly. Plant AS is believed to assemble as a homodimer (Rognes, 1975, Phytochemistry, 14:1975–1982). In leaf mesophyll tissue where wild-type As is not normally expressed, the glnΔAS1 form is able to self-assemble into homodimers and form an enzyme capable of generating asparagine. In phloem cells, however, glnΔAS1 subunits may co-assemble with wild-type AS subunits, thereby inactivating wild-type AS as a dominant-negative mutation (Herkowitz, 1987, Nature 329:219–222). In the glnΔAS1 plants, asparagine synthesized in leaf mesophyll cells may be unable to be transported to and loaded into the phloem and this could account for the poor growth phenotype of these transgenic lines. These observations highlight the specialization of cell-type function, and cell-specific gene expression of nitrogen metabolic genes and their impact on plant nitrogen metabolism.

8. DEPOSIT OF MICROORGANISM

The following microorganism are deposited with the Agricultural Research Culture Collection, Northern Regional Research Center (NRRL), Peoria, Ill. and are assigned the following accession numbers:

| Strain | Plasmid | NRRL Accession No. |
|---|---|---|
| *Escherichia coli*, Z3 | pZ3 | B-21330 |
| *Escherichia coli*, Z9 | pZ9 | B-21331 |
| *Escherichia coli*, Z17 | pZ17 | B-21332 |
| *Escherichia coli*, Z41 | pZ41 | B-21333 |
| *Escherichia coli*, Z54 | pZ54 | B-21334 |
| *Escherichia coli*, Z127 | pZ127 | B-21335 |
| *Escherichia coli*, Z167 | pZ167 | B-21336 |

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publication are cited herein, the disclosure of which are incorporated by reference in their entireties.

What is claimed is:

1. A transgenic plant having a gene construct comprising a nucleic acid encoding a nitrogen assimilation/metabolism enzyme operably linked to a plant promoter so that the nitrogen assimilation/metabolism enzyme is ectopically overexpressed in the transgenic plant, and the transgenic plant exhibits:

i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct, when the transgenic plant and the progenitor plant are cultivated under identical nitrogen non-limiting growth conditions, wherein the nitrogen assimilation/metabolism enzyme is glutamate 2-oxoglutarate aminotransferase.

2. The transgenic plant of claim 1, wherein the plant promoter is a strong, constitutively expressed plant promoter.

3. The transgenic plant of claim 2, wherein the plant promoter is CaMV 35S promoter.

4. A seed of the transgenic plant of any one of claims 1, 2, or 3, wherein the seed has the gene construct.

5. A progeny, clone, cell line or cell of the transgenic plant of any one claim 1, 2, or 3, wherein said progeny, clone, cell line or cell has the gene construct.

6. The transgenic plant of claim 1, wherein the glutamate 2-oxoglutarate aminotransferase utilizes ferredoxin as a reductant.

7. The transgenic plant of claim 6, wherein the gene construct comprises a plant glutamate 2-oxoglutarate aminotransferase gene.

8. The transgenic plant of claim 1, wherein the glutamate 2-oxoglutarate aminotransferase utilizes NADH as a reductant.

9. The transgenic plant of claim 8, wherein the the gene construct comprises a plant or *E. coli* glutamate 2-oxoglutarate aminotransferase gene.

10. The transgenic plant of claim 1, wherein the glutamate 2-oxoglutarate aminotransferase comprises a chimeric bifunctional enzyme comprising both ferredoxin and NADH glutamate 2-oxoglutarate aminotransferase activities.

11. The transgenic plant of any one of claims 1, 2, 3, 6, 7, 8 or 9 wherein the transgenic and progenitor plants thereof are selected from the group consisting of Arabidopsis, maize, wheat, rice, soybean, tomato, tobacco, carrots, potato, sugar beets, sunflower, yam, rape seed, and petunia.

* * * * *